United States Patent [19]
Adam et al.

[11] Patent Number: 5,483,968
[45] Date of Patent: Jan. 16, 1996

[54] METHOD AND APPARATUS FOR ANALYZING THE ELECTRICAL ACTIVITY OF THE HEART

[75] Inventors: Dan Adam; Ilia Vitsnudel, both of Haifa; Shlomo Gilat, Natania; Samuel Sideman, Haifa, all of Israel

[73] Assignee: Technion Research and Development Foundation Ltd., Technion City, Israel

[21] Appl. No.: 886,227

[22] Filed: May 21, 1992

[30] Foreign Application Priority Data

Jun. 25, 1991 [IL] Israel ............................................ 98613

[51] Int. Cl.$^6$ .................................................. A61B 5/0432
[52] U.S. Cl. .................................................. 128/696
[58] Field of Search .................................... 128/696, 699, 128/702, 710

[56] References Cited

U.S. PATENT DOCUMENTS

| | | | |
|---|---|---|---|
| 4,665,485 | 5/1987 | Lundy et al. ............................ | 128/710 |
| 4,924,875 | 5/1990 | Chamoun ................................. | 128/696 |
| 4,974,598 | 12/1990 | John ......................................... | 128/696 |
| 5,046,504 | 9/1991 | Albert et al. ............................ | 128/710 |
| 5,146,926 | 9/1992 | Cohen ..................................... | 128/710 |
| 5,161,539 | 11/1992 | Evans et al. ............................ | 128/696 |

*Primary Examiner*—William E. Kamm
*Attorney, Agent, or Firm*—Benjamin J. Barish

[57] ABSTRACT

A method and apparatus for analyzing the electrical activity of the heart by Body Surface Potential Mapping (BSMP) in which an array of electrodes are applied over the thoracic region of a subject's body for producing measurements of the electrical signals generated in the thoracic region, and the measurements are processed for indicating certain electrical events in the subject's body. The array of electrodes are utilized to measure only the times of crossing of the electrical signals over a preset threshold.

17 Claims, 15 Drawing Sheets

STAGE 1: CONSTRUCTION OF ORTHONORMAL EXPANSION BASIS

STAGE 2: RECONSTRUCTION FROM LC

FA490 (QRS Complex) FA490 (QRS Complex)

original reconstruction

ST820 (QRS Complex) ST820 (QRS Complex)

original reconstruction

METHOD AND APPARATUS FOR ANALYZING THE ELECTRICAL ACTIVITY OF THE HEART

The present invention relates to a method and apparatus for analyzing the electrical activity of the heart, and particularly to a method and apparatus which does this by Body Surface Potential Mapping (BSPM).

BACKGROUND OF THE INVENTION

BSPM (Body Surface Potential Mapping) is a relatively new technique for the study and analysis of the electrical activity of the heart. In contrast to the standard ECG technique, in which the heart activity is measured by the 12 standard leads, the information about the heart in the BSPM method is obtained from all over the thorax, by placing an array of many electrodes (usually 120–240 in number) on the body of the subject. Since the data is recorded simultaneously from all electrodes, this technique is capable of providing sensitive information (see [1] and its references) concerning electrical events in the heart and enables better spatial resolution in locating the cardiac generators [2,3].

However, despite the improved spatial resolution and sensitivity of the BSPM method, utilization of BSPM is limited to a small number of laboratories. Three main reasons were pinpointed by Mirvis in [1]:1) There are various alternative techniques, such as echocardiography, CT and MRI, which provide noninvasively useful clinical information; 2) The technical complexity and the price of custom-designed multielectrode BSPM system, which includes sophisticated multiplexing, amplification, filtering, sampling and storage units; 3) The vast amount of raw data obtained by BSPM, which requires long processing times as well as a new form of graphical representation.

Many studies explored partial solutions for the two last problems. Almost all studies take advantage of the statistical properties of the electrocardiographic signals, in order to reduce the system complexity and the amount of measured data.

The statistical properties of the ECG signals were studied by Favella et al. in [4], who showed that the electrical potentials projected on the thorax may be treated as samples of a stochastic process defined by the autocorrelation kernel:

$$R(z,z')=E[(F(z)-f(z)) (F^*(z')-f^*(z'))] \quad (1)$$

where *—is complex conjugate, z=(x,y)—are coordinates on the thorax, F(z)—is a random field, with some probability measure, E[ ]—is the expectation of an ensemble of samples at the moment $t_0$ and $f(z)=E[F(z)]$.

Eigenfunctions of R (z,z') are usually used in compression protocols of BSPM data. Horan et al. [5], studied the ECG waveform by the means of Principal Factor Analysis. Ahmed and Rao compared different ECG compression methods based on orthogonal expansions and found that when reconstructing the signal from 16 coefficients of Karhunen-Loeve (K-L) expansion, the mean square error is approximately two times lower than by Discrete Cosine Transform [6]. Compression of potential maps in the spatial domain, was investigated by Lux et al. [8]. Their results show that the reconstruction of a map is obtained by means of 12 eigenfunctions for the QRS period and by 30 eigenfunctions for the whole QRST with up to 2% RMS error, whereas temporal compression [9] of the spatially reduced BSPMs, required 18 expansion coefficients.

One of the most difficult problems in BSPM compression by the expansion on an eigenfunction basis, is the need to compute and decompose very large covariance matrices. Uijen et al. [10], used the SVD method and showed an efficient way to circumvent this computation obstacle. In their study, the authors used only 36 first coefficients of K-L decomposition for the reconstruction of the BSPM within the 73 µV RMS error limit during the QRS phase.

Statistical methods, other than K-L expansion, are utilized in a sequential algorithm, based on covariance matrix analysis, for finding the optimal locations of a reduced electrode set on the thorax [11]. Thirty electrodes are used to produce an estimation (by the linear transform) of a whole rectangular electrode grid within the correlation of 0.98 and the RMS error of the order of the system noise.

BSPM compression has also been performed on the deterministic orthogonal basis. A more extended function basis is required to produce the same reconstruction quality, but other advantages may be gained. Balossino et al. [12] utilize a basis of spherical harmonies, where rotational invariance of the measurement system is achieved. Thus the measurement is less sensitive to the directional alignment of the electrodes, which are usually mounted on a jacket worn by the patient. The body size also becomes an invariant parameter. This reduces the drawbacks of applying the BSPM in the clinic.

In the reports described above, the BSPM measurement is simplified and its data compressed by reducing the number of electrodes, while allowing some predefined small statistical error. Still, the simplified system includes rather complex analog electronic units. Furthermore, the information content provided by each one of the remaining electrodes becomes critical, therefore requiring a more accurate and expensive instrumentation.

The present invention describes a new approach based on implementing level-crossing electrodes for simplifying the BSPM measurement system and concurrently compressing the data. To utilize this approach a novel algorithm for reconstruction from level-crossings (LC) is developed. The electrodes in the suggested system are used only for detecting the times when the incoming ECG signal crosses some given voltage level. This partial data provides information for reconstruction of the original BSPM. As shown later, the LC data is sufficient for the reconstruction of the BSPM and therefore the complexity of the measurement system may be significantly reduced. The compression of the BSPM is achieved as well, since the level-crossing electrodes provide only a few samples per cardiac cycle for each electrode.

BRIEF SUMMARY OF THE INVENTION

According to one aspect of the present invention, there is provided a method of analyzing the electrical activity of the heart by Body Surface Potential Mapping (BSMP), in which method an array of electrodes are applied over the thoracic region of a subject's body for producing measurements of the electrical signals generated in the thoracic region, and the measurements are processed or indicating certain electrical events in the subject's body; characterized in that the array of electrodes are utilized to measure only the times of crossing of the electrical signals over a preset threshold.

According to another aspect of the present invention, there is provided a method of analyzing the electrical activity of the heart by BSPM, in which the processing of the measurements includes the following steps:

(a) estimating the covariance matrix of random processes from the measurements by the array of electrodes;

(b) decomposing the covariance matrix into the eigenfunction basis;

(c) evaluating, from a partial set of the measurements for the respective subject, the coefficnt of a linear combination of computed eigenfunctions; and (d) expanding the computed eigenfunctions to obtain a complete reconstruction of the BSPM.

According to further features in the preferred embodiment of the invention described below, the reconstruction is performed by dividing the array of electrodes into a plurality of intermittent grids, and utilizing a corresponding number of the threshold levels, one for each of the grids; preferably, there are four intermittent grids, and four threshold levels are utilized, one for each of the grids.

The invention also provides apparatus for analyzing the electrical activity of the heart by BSPM mapping in accordance with the foregoing methods.

Further features and advantages of the invention will be apparent from the description below.

DESCRIPTION OF THE DRAWINGS

The invention is herein described, by way of example only, with reference to the accompanying drawings, as follows.

(a) Infinite resolution sampling.

(b) Simulation of "exact" level-crossing instant measurement.

(c) Approximation of level-crossing instant by the nearest sampling point.

(d) Extreme situation where approximation of level-crossing instant (like in (c)) is erroneous.

Figure 5:
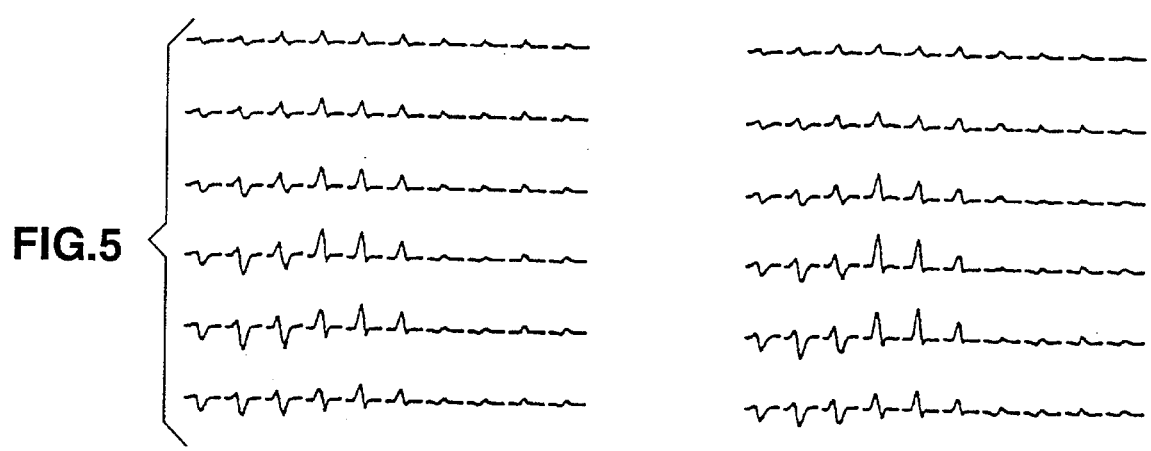

FIG. 5. Example of original (left) vs. reconstructed (right) waveforms of the QRS portion for a representative normal subject. The RMS error is 70 $\mu V$ and the correlation is 0.93. Only the 60 most significant electrodes are shown. $-100$ $\mu V$ threshold level was used for the level-crossing instants measurement.

Figure 6:
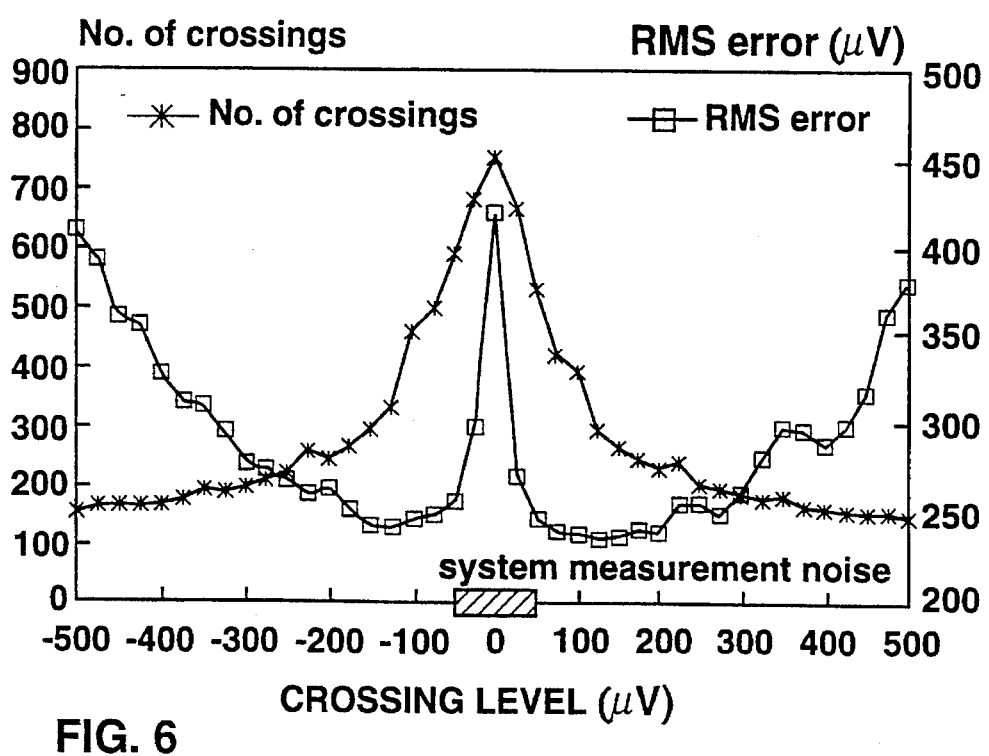

FIG. 6. BSPM reconstruction error (RMS) and number of crossing points of a representative normal subject as a function of the threshold set for measuring the level-crossing instants.

Figures 7, 8:
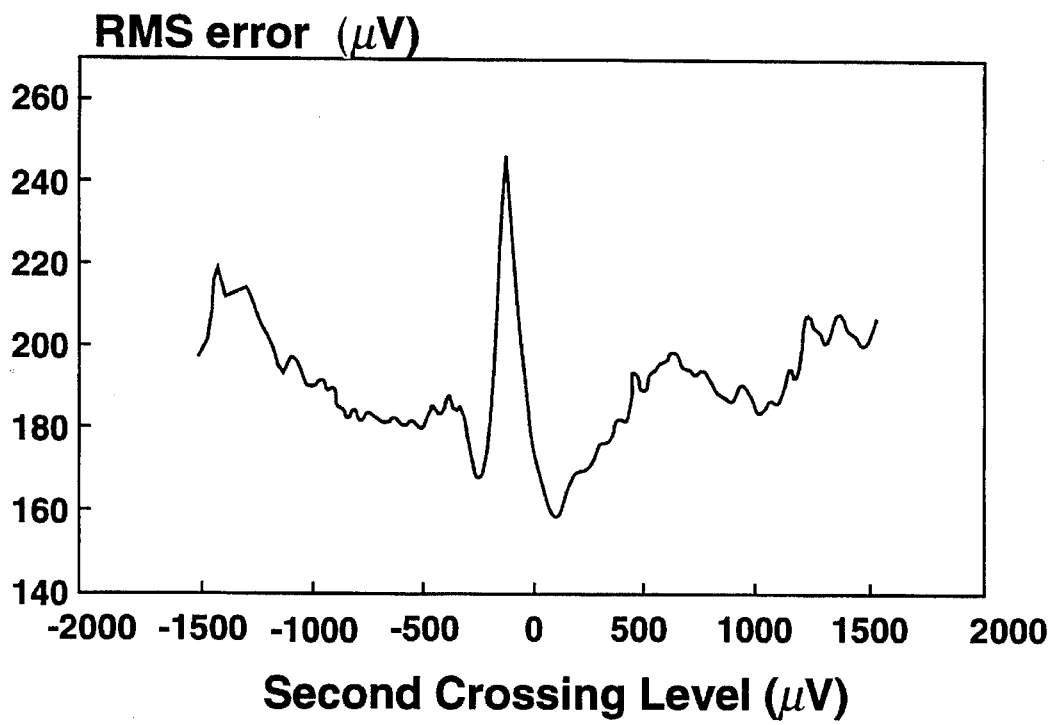

FIG. 7. BSPM reconstruction error (RMS) of a representative normal subject, when the voltage threshold for every second electrode is modified between $-1500$ $\mu V$ to $1500$ $\mu V$, in 50 $\mu V$ steps. All other electrodes measure at the original level of $-100$ $\mu V$.

FIG. 8. The arrangement of the preferred net of Level-Crossing electrodes, divided into four subsets of 45 electrodes, each set to a different threshold level ($\pm 100$ $\mu V$, $\pm 500$ $\mu V$).

Figure 9:
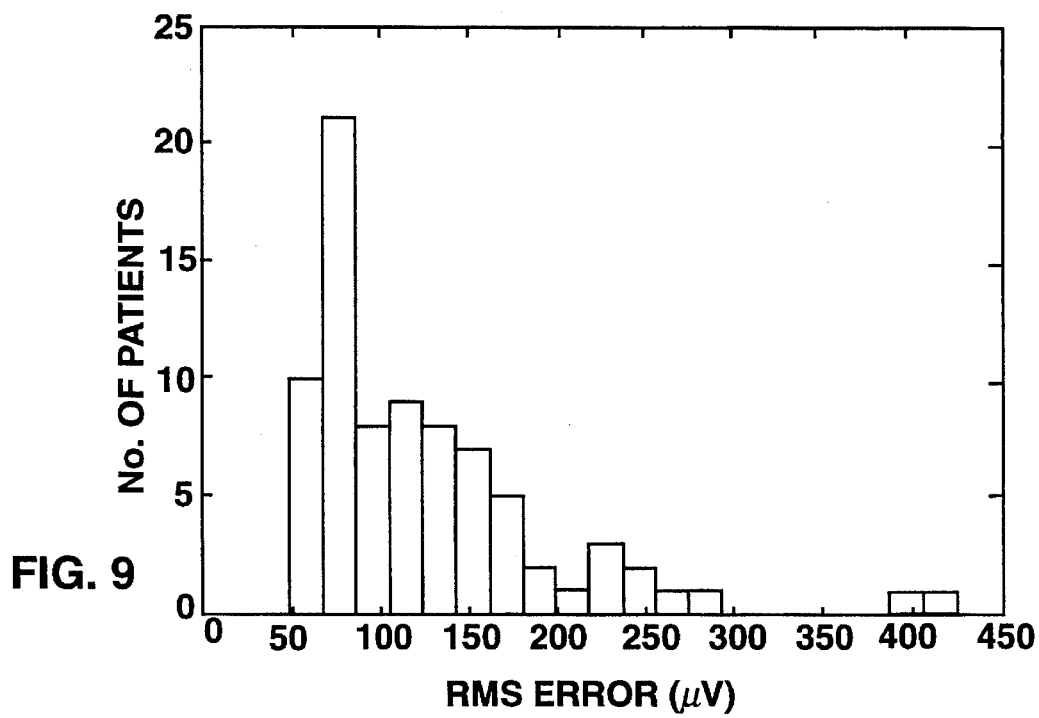

FIG. 9. The histogram showing the distribution of RMS reconstruction error for all subjects from the test set.

Figure 10:
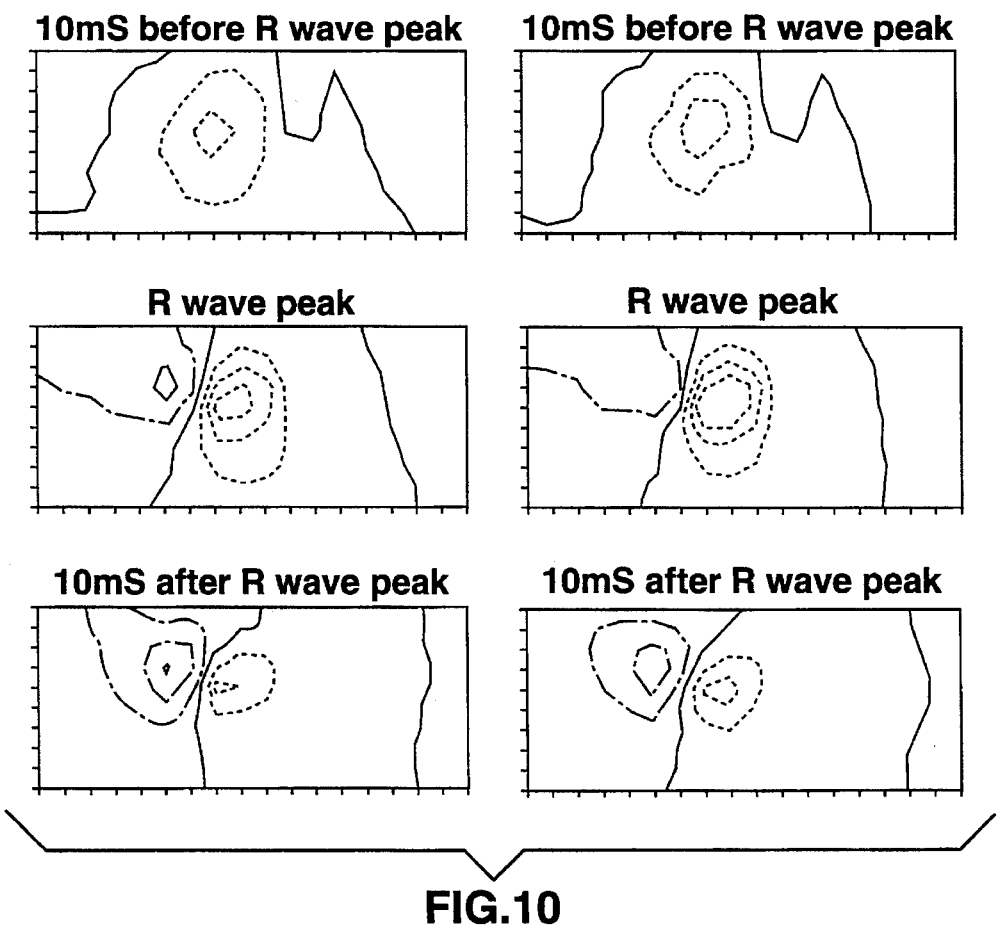

FIG. 10. Examples of original (left) vs. reconstructed (right) maps from a representative normal subject, at certain moments during the QRS phase. The reconstruction was performed on a basis of 80 eigenfunctions, with the net of electrodes measuring the level-crossing instants arranged as in FIG. 8.

Figure 11:
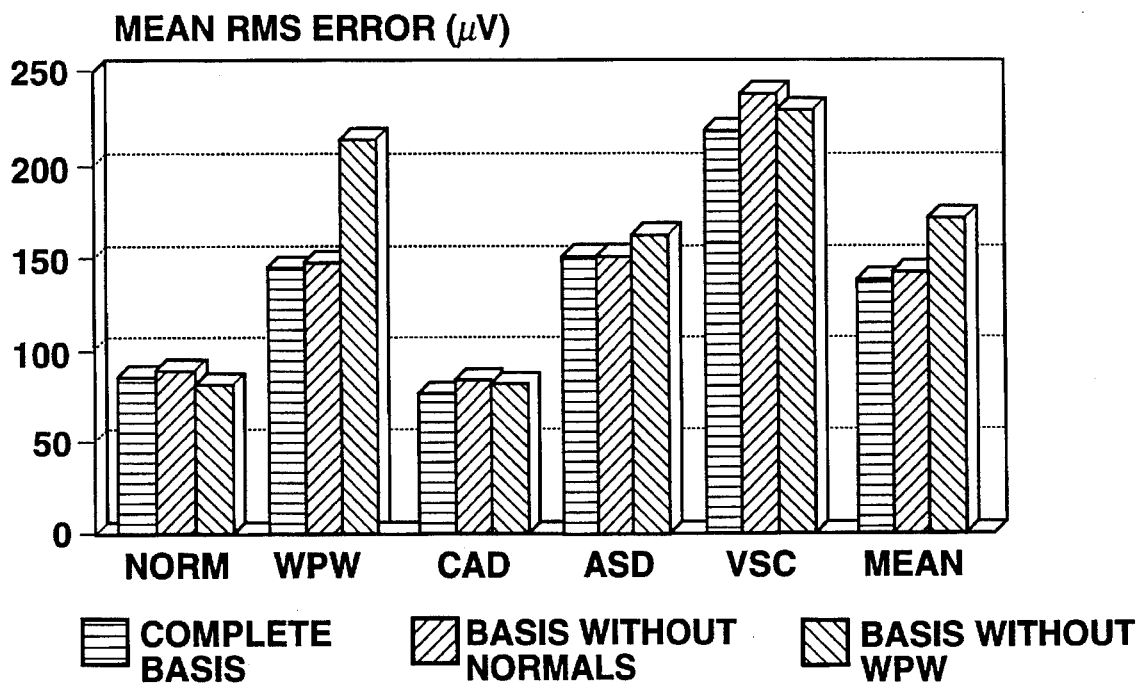

FIG. 11. Average BSPM reconstruction error (RMS), for the various groups of pathologies in the test set, and the effects of eliminating certain pathologies from the training set. The first column in each group represents reconstruction based on the entire training set, the second column—when the training set does not include normals, and the third column—the training set does not include subjects diagnosed as WPW.

Figure 12:
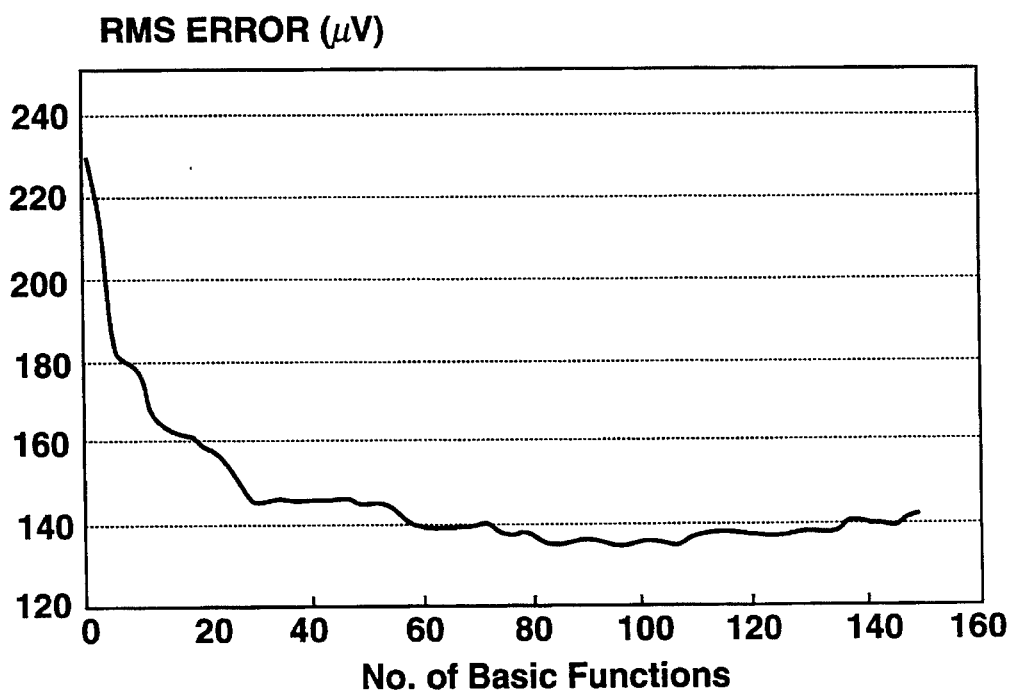

FIG. 12. Average RMS reconstruction error, calculated for the whole test set, as a function of the number of eigenfunctions used.

Figure 13:
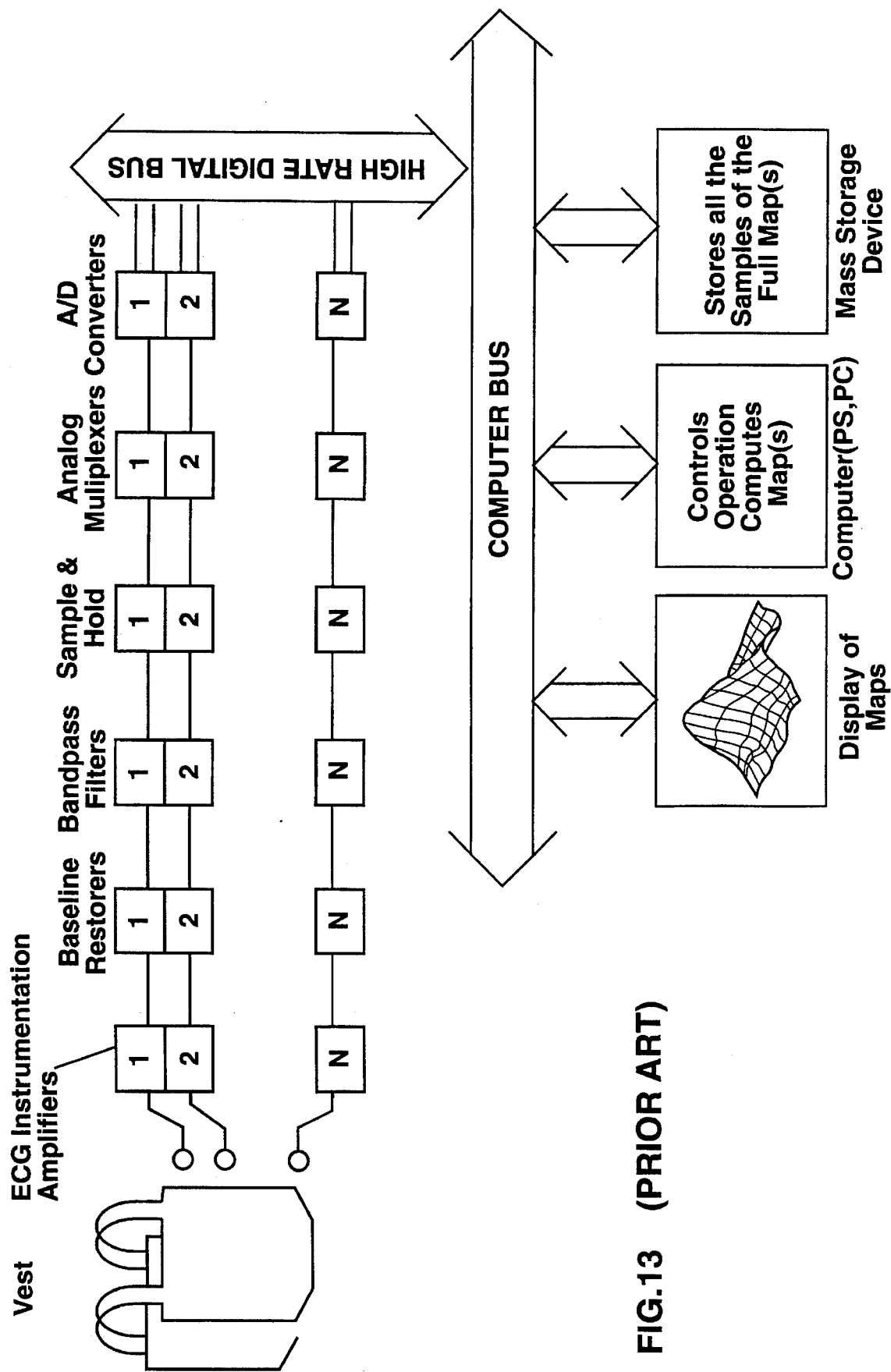

FIG. 13. Block diagram of an existing BSPM system, including the analog stages which may be replaced by the novel system.

Figure 14:
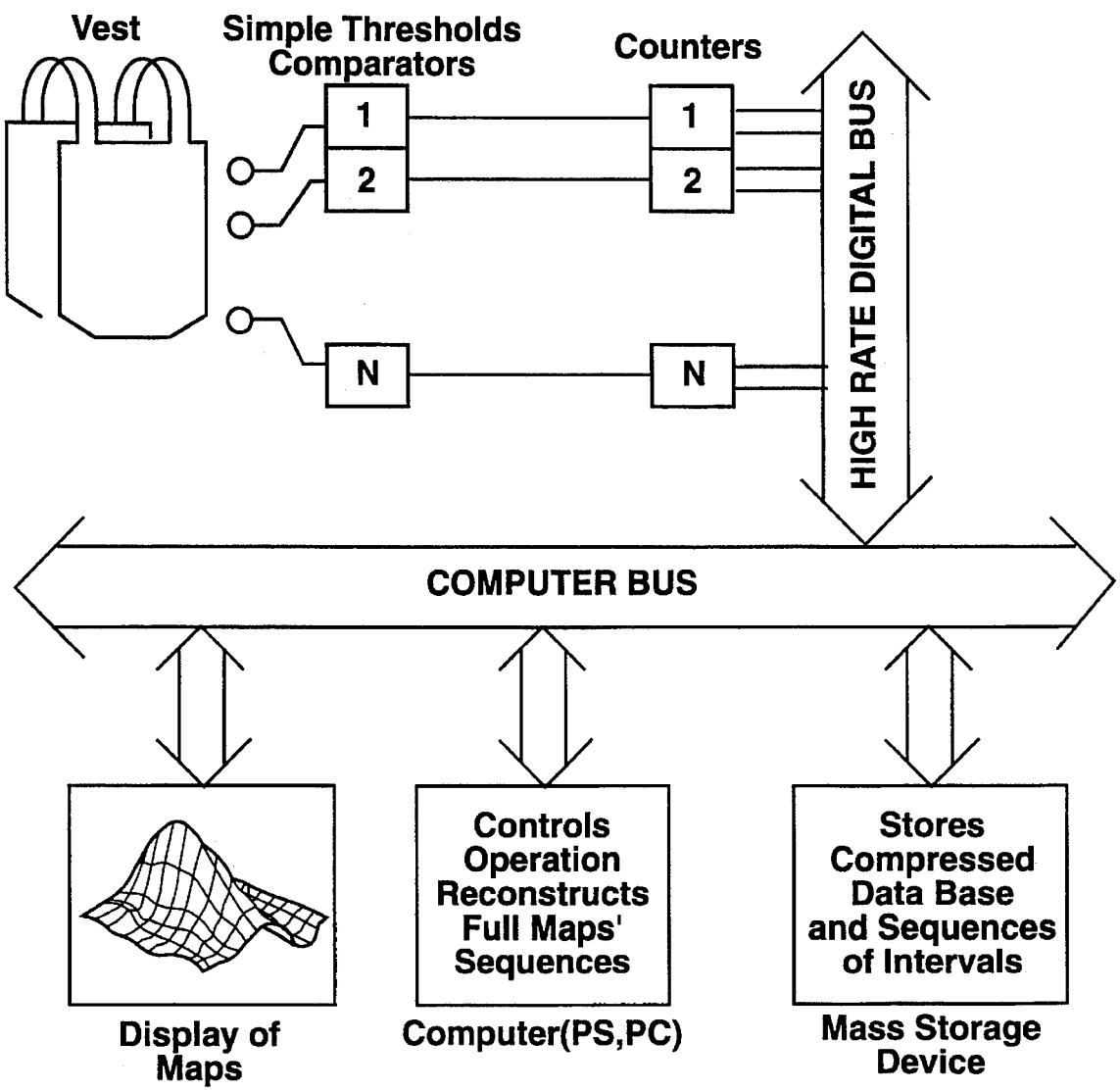

FIG. 14. Block diagram illustrating a BSPM measurement system in accordance with the present invention, detailing the simplified analog parts.

Figure 15:
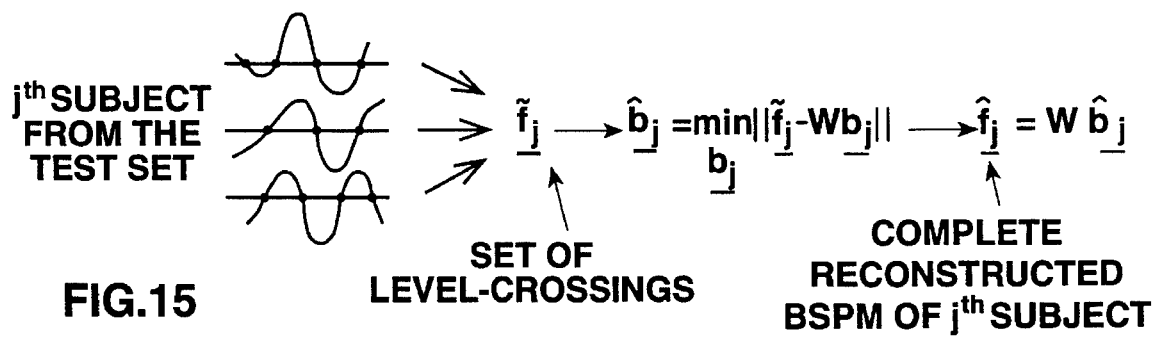

FIG. 15. More particularly illustrates the novel method in which each channel for the plurality of electrodes measures only the times of crossing of the electrical signals over a preset threshold, the values in the matrix W being stored as a compressed data base.

Figure 16:
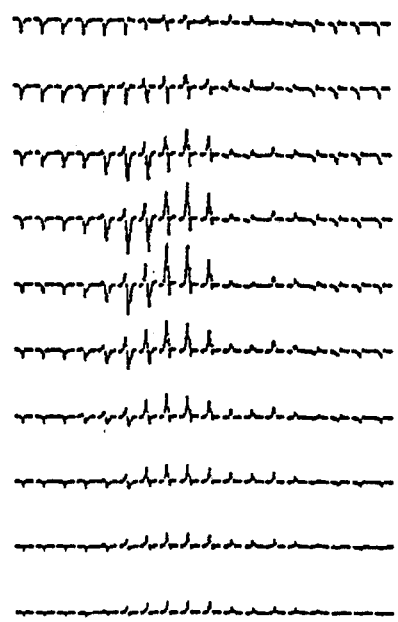
Figure 16:
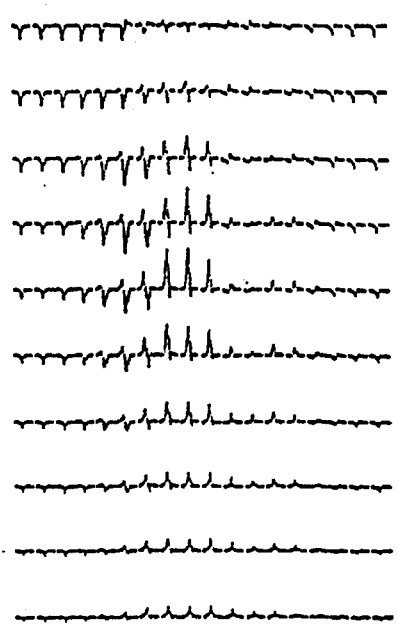
Figure 16:
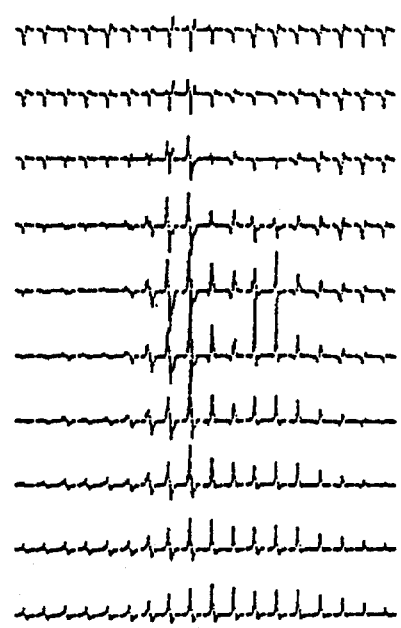
Figure 16:
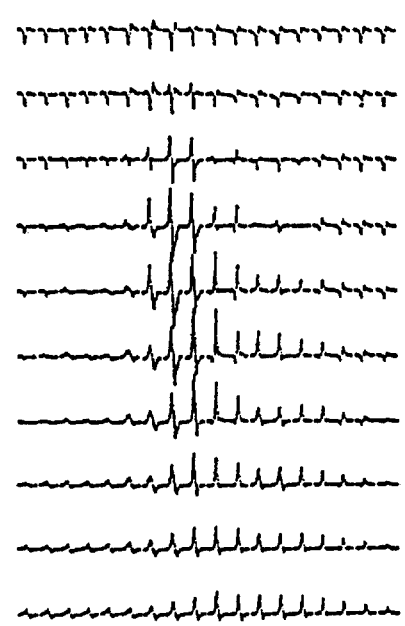

FIG. 16. Illustrates ECG potentials measured during one heartbeat by 180 electrodes around the thorax region for two subjects.

Figure 17:
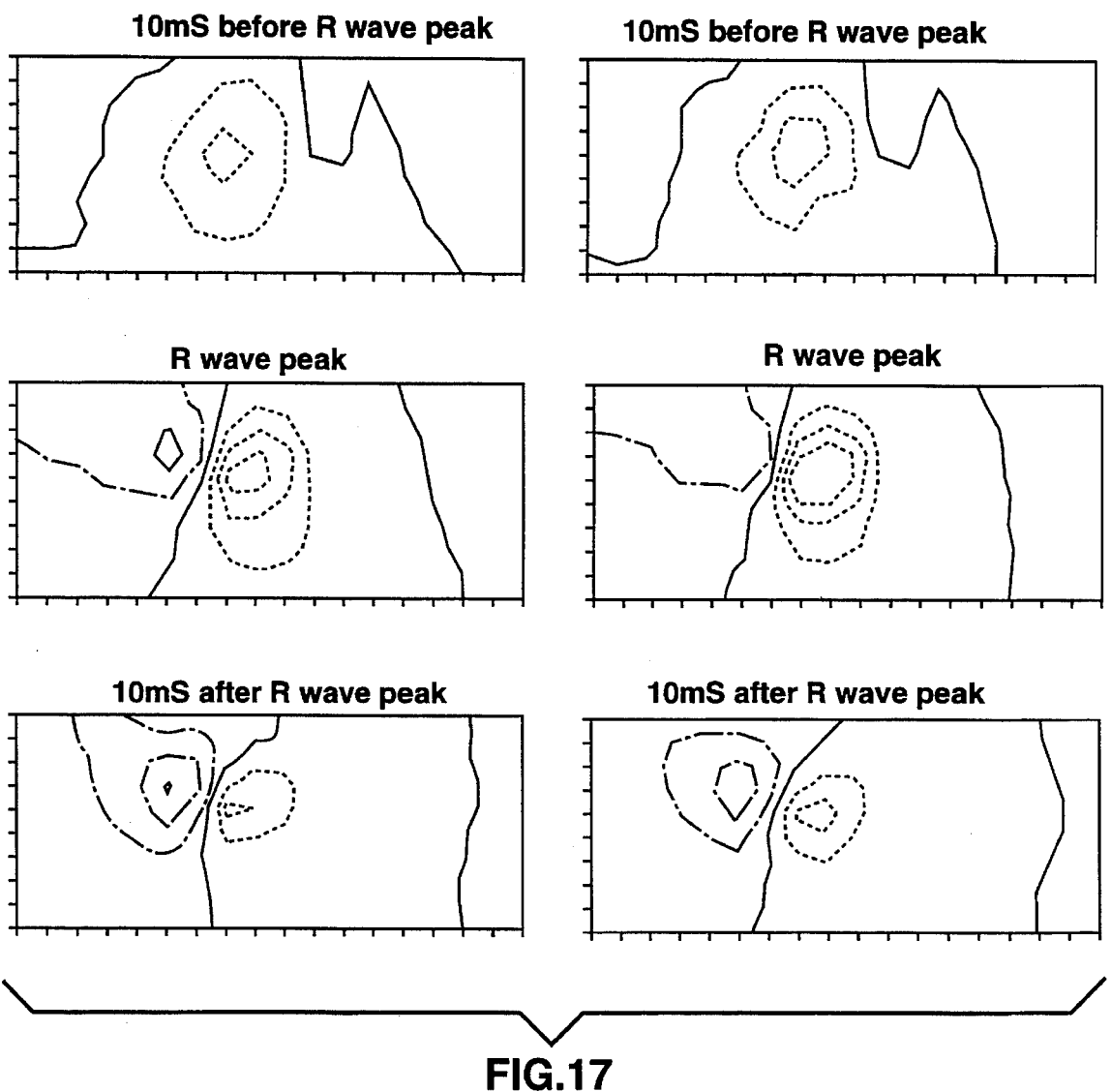

FIG. 17. Illustrates the sequence of three maps measured over the whole torso presented by 2-D isopotential lines.

Figure 18:
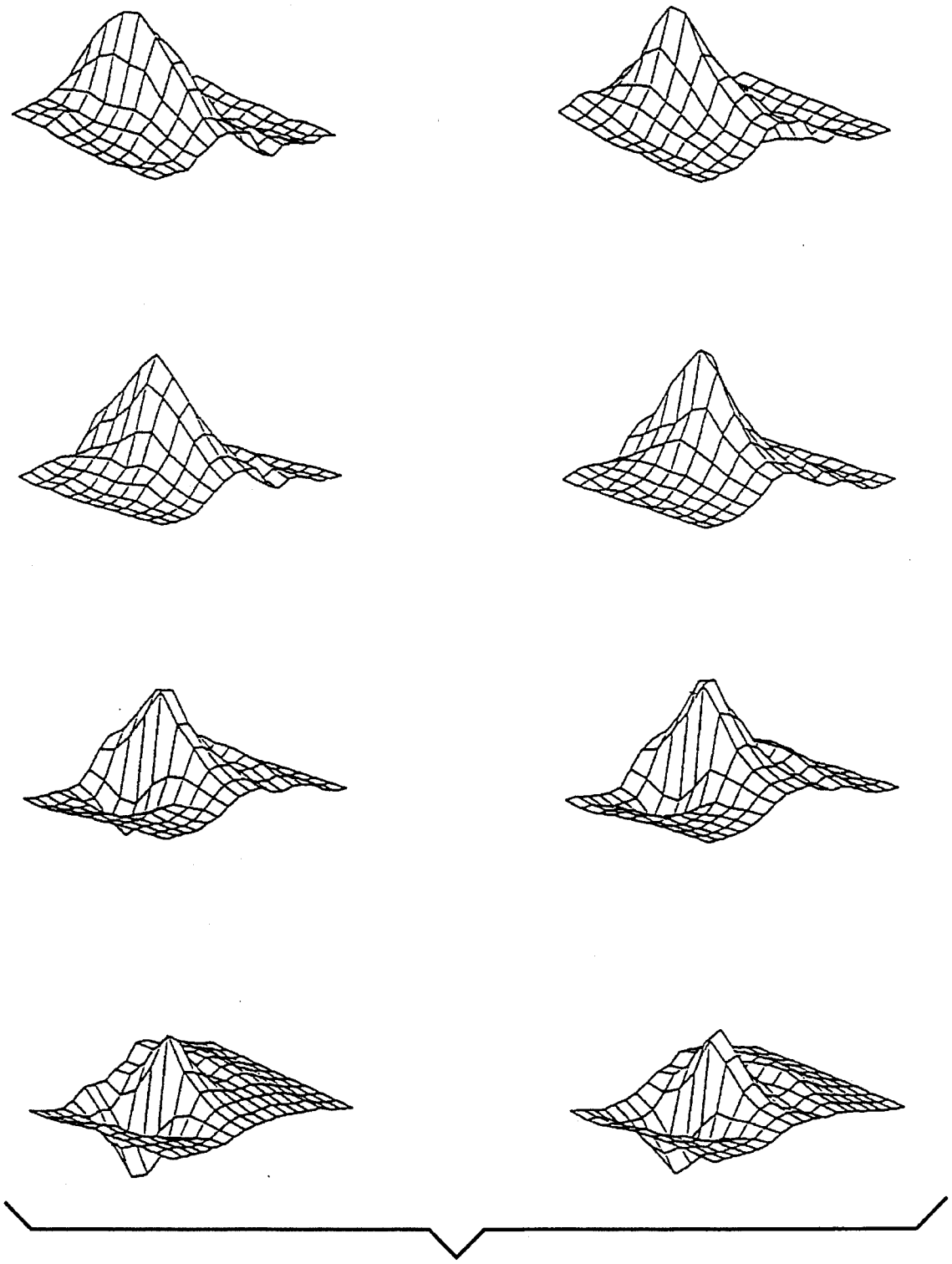

FIG. 18. Illustrates the sequences of four 3-D potential maps measured over the whole torso.

Figure 19:
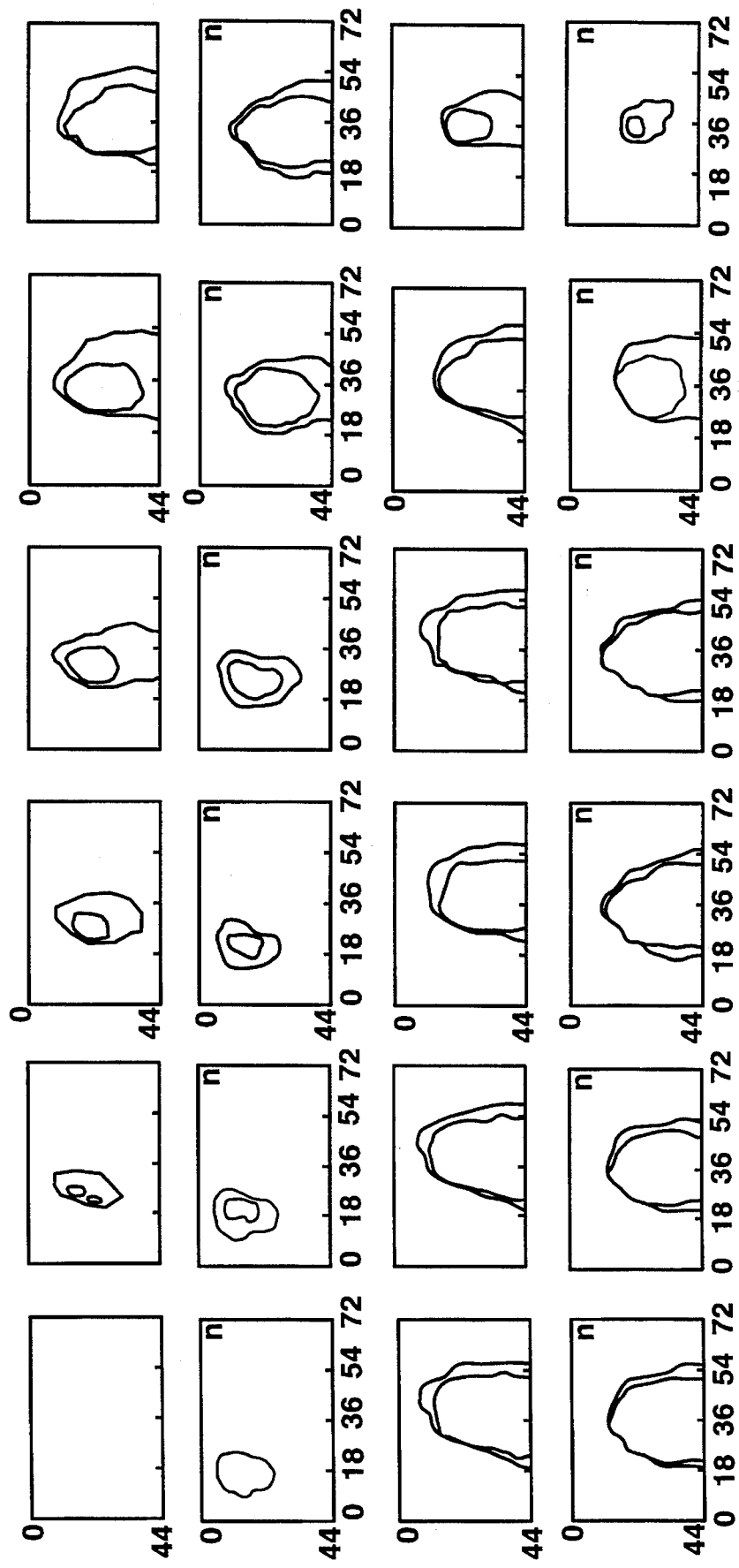

FIG. 19. Illustrates a typical annuli sequence calculated from original and/or reconstructed BSPM.

Figure 20:
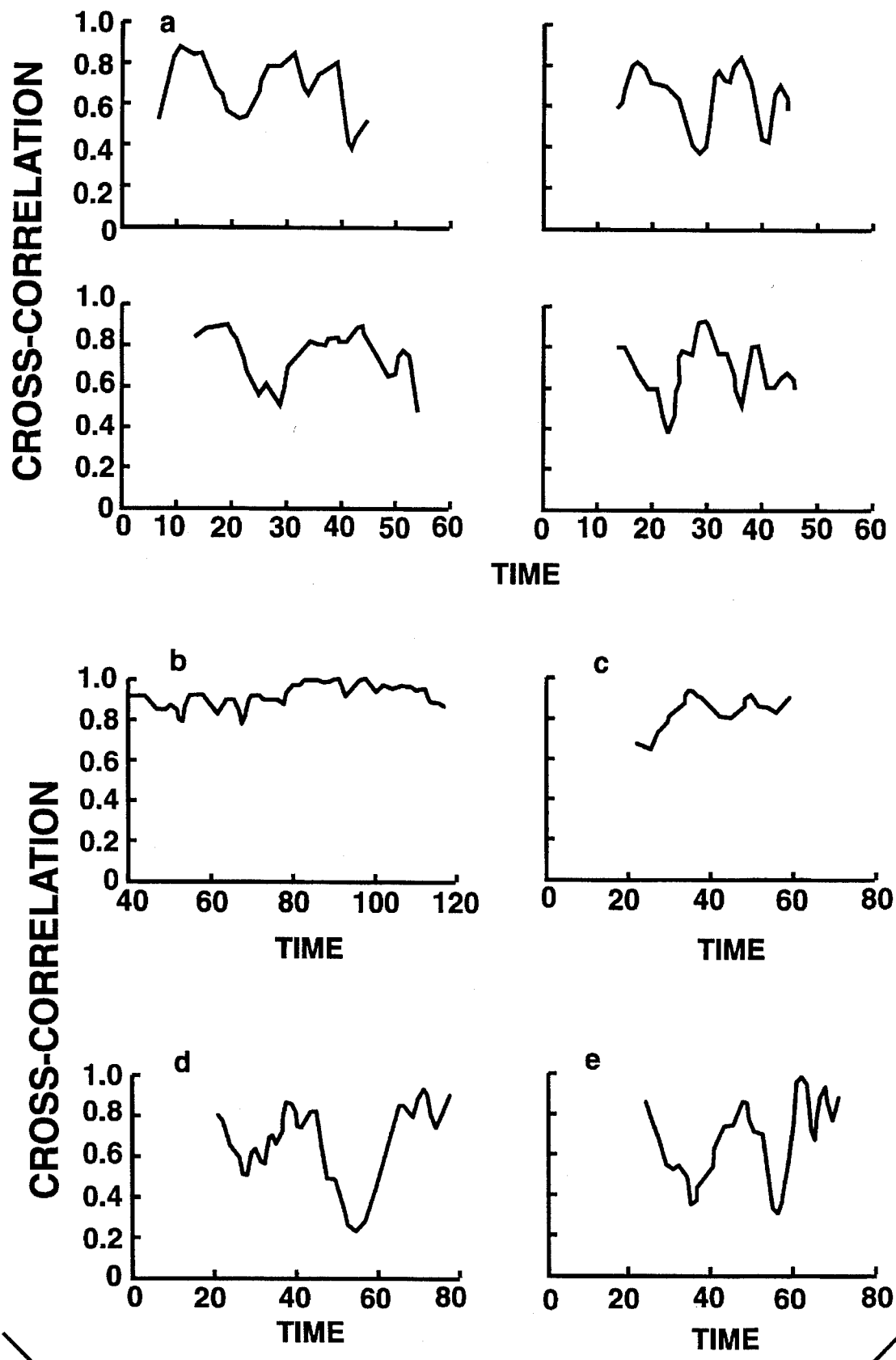
Figure 21A:
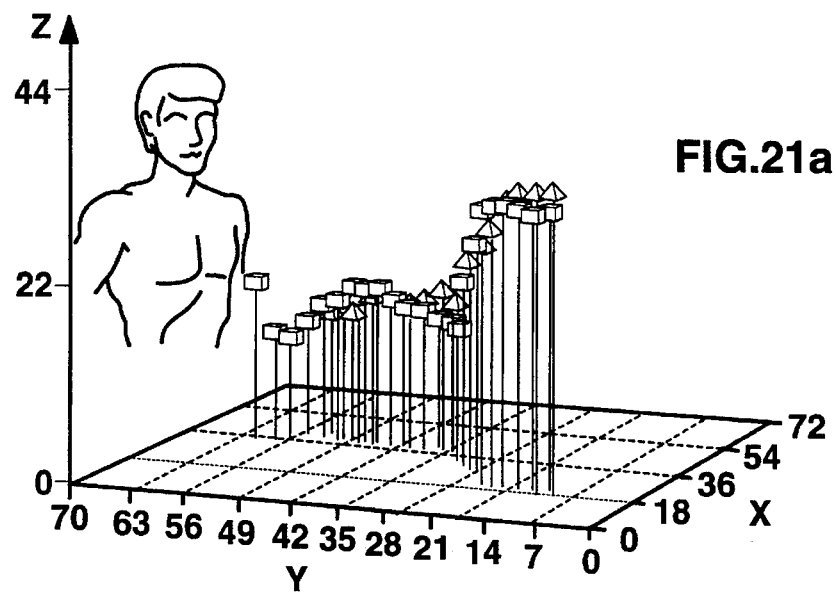
Figure 21B:
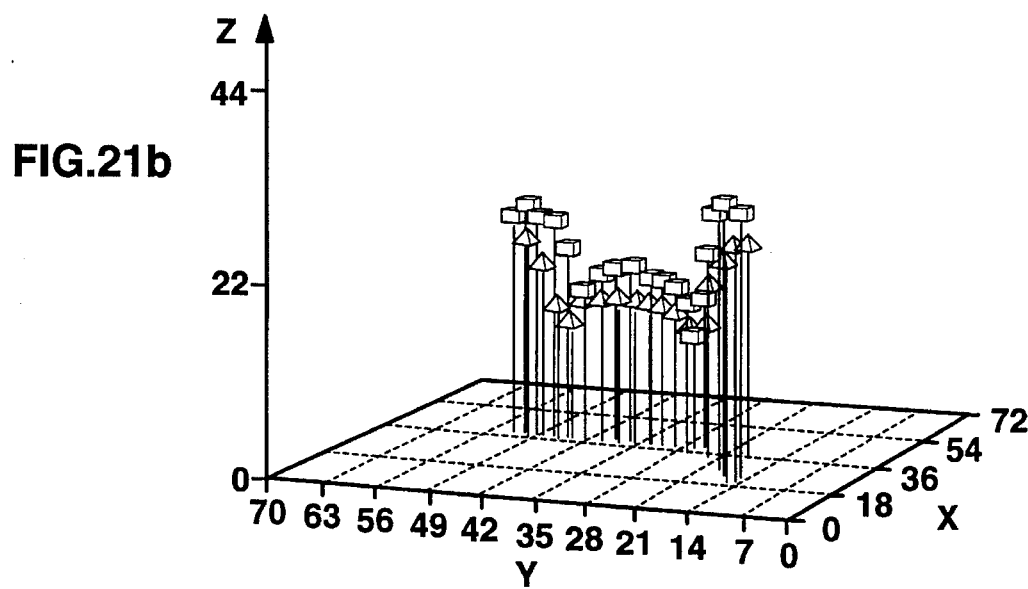
Figure 21C:
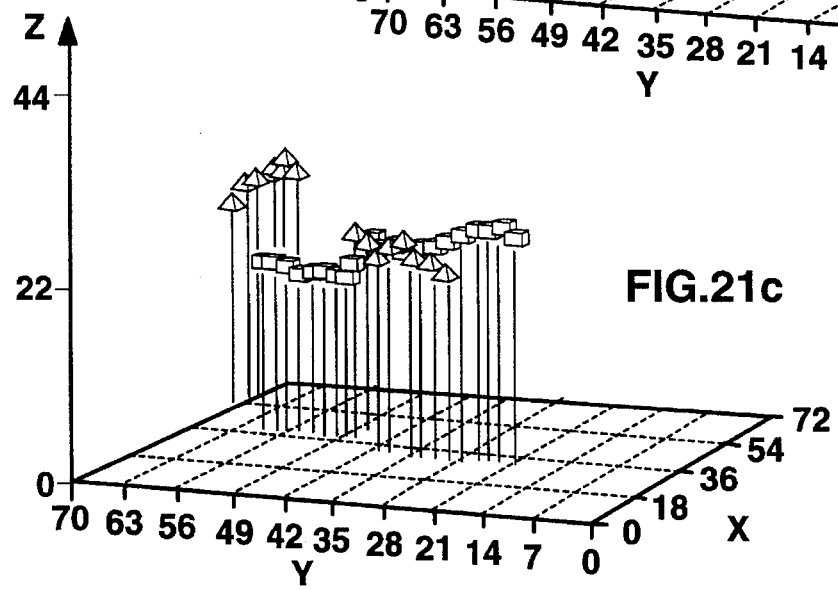
Figure 21D:
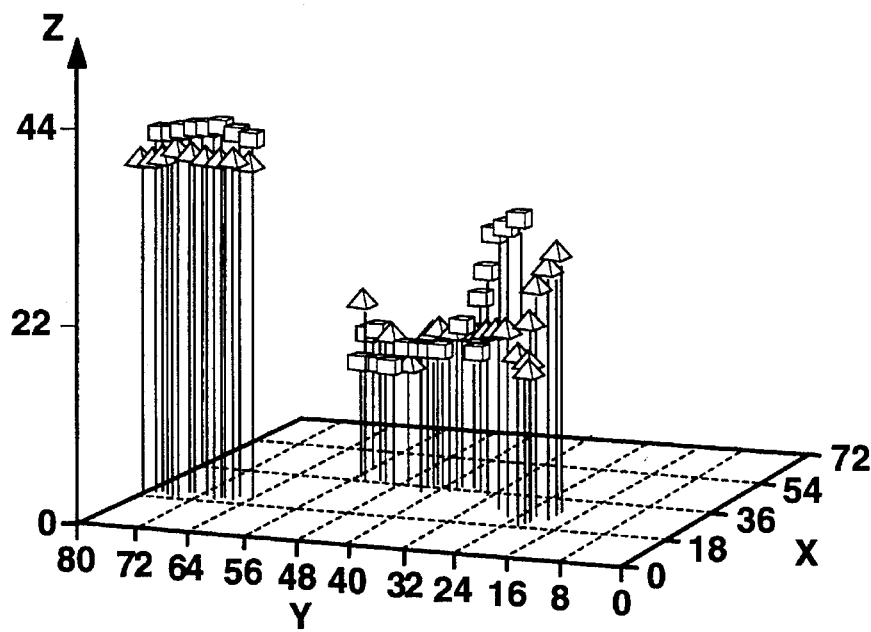
Figure 21E:
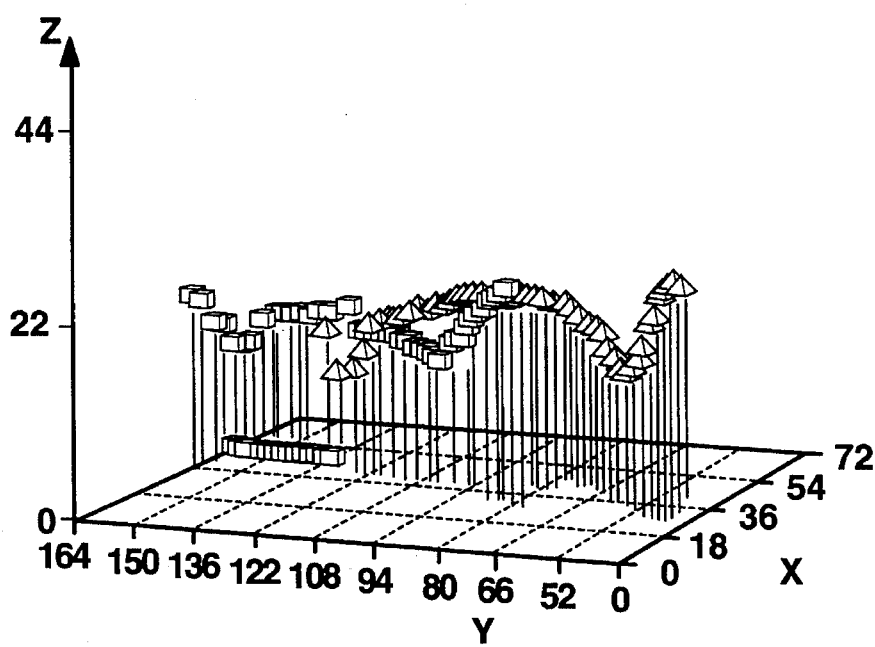

FIG. 20. Illustrates cross-correlation coefficients series as a function of time of the annuli sequence of FIG. 19.

FIG. 21a–21e. Illustrate features extracted from sequences of potential maps as measured over the whole torso.

REFERENCE METHODS FROM ZERO-CROSSING

The problem of signal reconstruction from its zero-crossings (ZC) interested many investigators in various fields of science. Initial attempts were made in the field of communications and have concentrated on one-dimensional signal reconstruction [14]. The main efforts have been directed at identifying satisfactory conditions for signal reconstruction and algorithms which guarantee stable and unique reconstruction. In most of the reports, the investigators make use of complete functions (analytical everywhere), based on the fact that band-pass limited function is complete and therefore is defined by its zeroes (complex and real) within the scaling and exponential factor [15]. Moreover, any real function is well-defined by its zero-crossings if all of its zeroes are real [16]. Thus, efforts have concentrated on finding conditions under which signals are guaranteed to have only real zeroes, or signals in which the rate of real zeroes is higher in some respect than the information content provided by those signals. Logan [17], defined a new class of band-limited signals which are uniquely represented by their zero-crossings (within a scaling factor).

However, most of the real, band-pass limited signals do not satisfy all the analytical restrictions imposed by these methods, and therefore cannot be uniquely represented by their ZC.

Reconstructions from zero-crossings in multidimensional domains have produced more significant results. Major contributions have been made in image processing, where the signals are mostly two-dimensional. Rotem & Zeevi [18] expanded the theoretical work of Logan [17], for band-pass limited signals in 2-D, and succeeded to construct a practical algorithm for reconstruction from zero-crossings.

Though several reports describe direct extensions of one-dimensional approaches to multidimensional problems, the effective handling of 2-D signals is based on a different property of the multidimensional problem. Zero-crossings of 2-D data create 2-D contours rather than discrete sampling points as in 1-D. As the ZC of 2-D data are represented by trajectories, and the ZC of 3-D by surfaces, the original multidimensional data produces, at least theoretically, an infinite number of zero-crossing sampling points. Thus, in some cases, the sampling rate restrictions imposed by the Nyquist theorem are satisfied.

Two major approaches are used for reconstruction from ZC in multidimensional domains. The first approach, proposed by Curtis et al. [19,20], is based on the direct application of the 2-D Fourier Series Expansion. The expansion coefficients, which constitute a set of unknowns of linear system of equations, are estimated from the set of measured ZC. A reasonable reconstruction is obtained when the number of ZC points is 4 times the number of Fourier coefficients. For such an overdeterminicity, the problem is then solved by a least squares method. This method assumes the availability of a periodic, band-limited image, which leads to finite number of unknowns and requires precise measurements of ZC.

The second approach to reconstruction from ZC, uses iterative procedures of Gershberg-Saxton type algorithm [20,21,22]. This algorithm operates by imposing restrictions on reconstructed signals, in the signal and frequency domains, for each iteration step, coercing them to convert to the original signal. The transition between domains is made by the means of DFT. The frequency domain restriction imposed on a signal would serve as a low-pass filter, e.g. limiting the reconstructed signal to the frequencies contained in the original signal. In the signal domain the restriction is imposing the correct sign in places where there are sign differences between measured and reconstructed signals.

The above approaches impose very strict limitations for practical usage. In the case of 2-D BSPM, ZC points could be approximated very roughly, because of finite spatial placement of electrodes, and, in the 3-D case, spectral information of BSPM cannot be limited to a sufficiently small number of coefficients.

Accordingly, these methods for signal reconstruction from its ZC described above, cannot be implemented for BSPM reconstruction.

In the next section we propose a different reconstruction method, which is based on utilization of intrinsic properties of BSPM by means of signal statistics, therefore providing an additional constraint, limiting the reconstruction procedure to a certain class of signals.

THE PROPOSED METHOD

Figure 1:
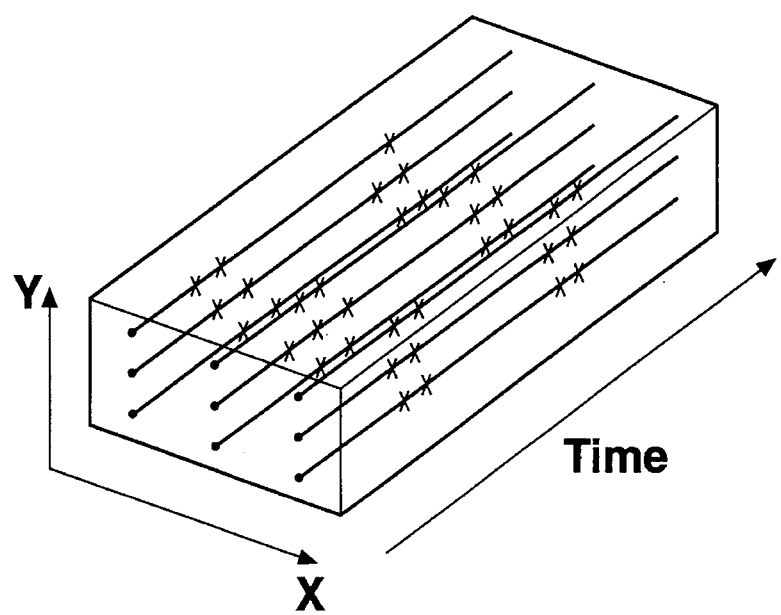
FIG. 1. Level-crossing instants produced when the threshold is crossed by the ECG voltage measured by each individual electrode. These instants are exactly those when a three-dimensional BSPM surface crosses the same threshold along the time axis.

The overall body surface electrocardiogram distribution is treated here as a three-dimensional random process, varying both in space and time and defined on some probability measure. A realization of this process (i.e. potentials that can actually be measured over the thorax) is denoted as f(x,y,t), where (x,y) are thorax spatial coordinates and t is the time coordinate, limited to one heart beat. In this case, the BSPM may be presented as a continuous surface. When level-crossing (LC)* is performed on this surface, using electrodes fixed over the thorax, LC values are found as the instants when the BSPM surface crosses some given threshold level along the time axis. This situation is depicted in FIG. 1. Those crossing times constitute a sampling set of the BSPM function.

for the practical purpose of reconstruction of the BSPM, it is more useful not to constrain the threshold level to zero, rather to set some other level. Therefore, the more general name LC (level-crossings) is used instead of the more limited ZC.

Since every level-crossing electrode measures only a few points during heart beat, the sampling set of LC of a BSPM is rather quite small. Therefore, to reconstruct the original BSPM from the LC information, the BSPM should be represented in a very compact way. As mentioned earlier, the BSPMs are viewed as samples of a random process, so they comprise a very specific restricted group in the whole signal space. Such a group can be described by a small number of parameters.

By using the Karhunen-Loeve transform approach [4], it is possible to decompose the autocorrelation kernel of a random process into the eigenfunction basis, and then represent the original BSPM function on it. As the resulting eigenfunction basis is characteristic to the random process, fewer functions are required for reconstruction of the original waveform than in any other decomposition method. This feature facilitates a practical reconstruction algorithm from LC for BSPM signals.

Thus, our approach to the reconstruction of BSPM from level-crossings is: Stage 1, based on a set of complete measurements of BSPM, estimate the covariance matrix of random process and then decompose it into the eigenfunction basis. Stage 2, from partial set of LC measurements for a particular subject, evaluate the coefficients of linear combination of computed eigenfunctions and then expand them to obtain complete reconstruction of BSPM.

Stage 1: Construction of orthonormal expansion basis. The total 3-D BSPM is represented as a single vector similar to [10]: Suppose $f_i(x,y,t)$ of the $i^{th}$ subject is given in its discretized version as a matrix $F_i$ of p·t dimension, in which rows represent the ECGs and columns are (maps given as) p-dimensional surface maps, where surface maps are in turn written as vectors consisting of all electrode site measurements:

$$F_i = (m_1, \ldots m_t) \qquad (2)$$

Next, by stacking the columns of $F_i$ in one long column, a single vector $f_i$ of dimension (1·pt) representing the total BSPM of the $i^{th}$ subject is formed:

$$f_i = (x_1, \ldots x_{pt})^T \qquad (3)$$

Given a sample of N patients, a covariance matrix is estimated and then decomposed to produce the eigenfunctions basis. However, numerical evaluation of the eigenfunction is very extensive because of the enormous dimension of the covariance matrix (pt·pt). An effective calculation of eigenfunctions, based on the SVD method [23] is used here. If Q represents a matrix, composed of N patients, $$Q = (f_1, \ldots f_N) \quad (4)$$

hen Q could be decomposed as $$Q = WSZ \quad (5)$$

where W is a (p·t·N) matrix representing an orthonormal expansion basis, S is a (N·N) diagonal matrix containing the ordered singular values and Z is a (N·N) matrix.

In the case presented here, however, direct application of the decomposition in Eq. (5) can be made for the determination of the set of basis functions, given the complete training set of BSPM's recordings for N patients.

Stage 2: Reconstruction from LC. When the only BSPM measurements are the small set of LC points, it is not possible to apply Eq. (5) for reconstruction procedure and therefore another estimation method is considered. If we write the $j^{th}$ column of matrix SZ as $b_j$, than the next set of linear equations can be formed for the $j^{th}$ subject:

$$f_j = W b_j \quad (6)$$

Figure 2:
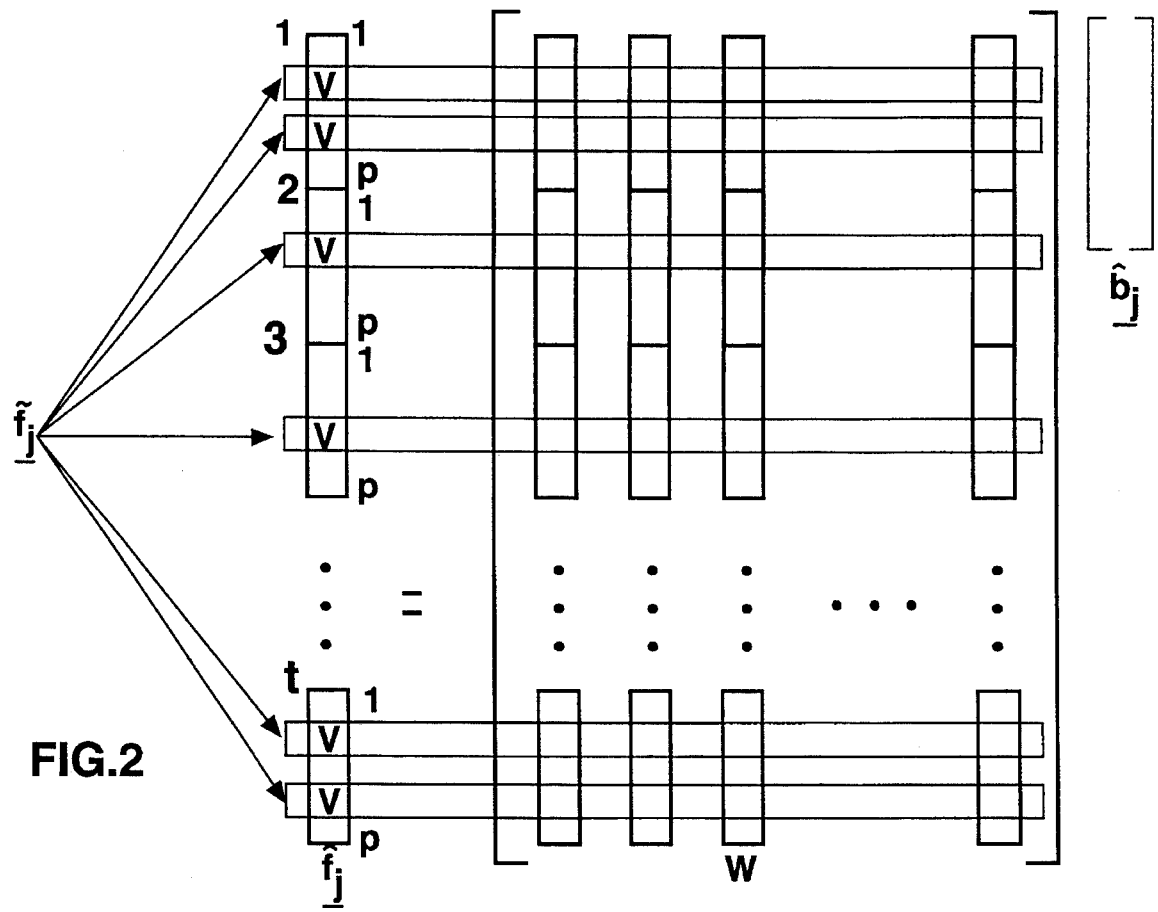
FIG. 2. Exemplification of set of equations (7). V—the threshold assigned to the specific electrode.

The number of equations is equal to p·t, but of these, only a small number, equal to the number of LC points, are available and well defined.

$$\tilde{f}_j = W b_j \quad (7)$$

where $\tilde{f}_j$ designates the set of LC measurements. FIG. 2 exemplifies construction of (7).

Equations in (7) constitute the system of linear equations which is solved for $b_j$ by the least squares method.

$$\tilde{b}_j = \min \| \tilde{f}_j - W b_j \| \quad (8)$$

Upon the estimation of the decomposition coefficients for a specific subject from the partial set of LC, the complete BSPM ($\hat{f}_j$) is constructed by using the whole set of equations in (6).

$$\hat{f}_j = W \tilde{b}_j \quad (9)$$

Figure 3:
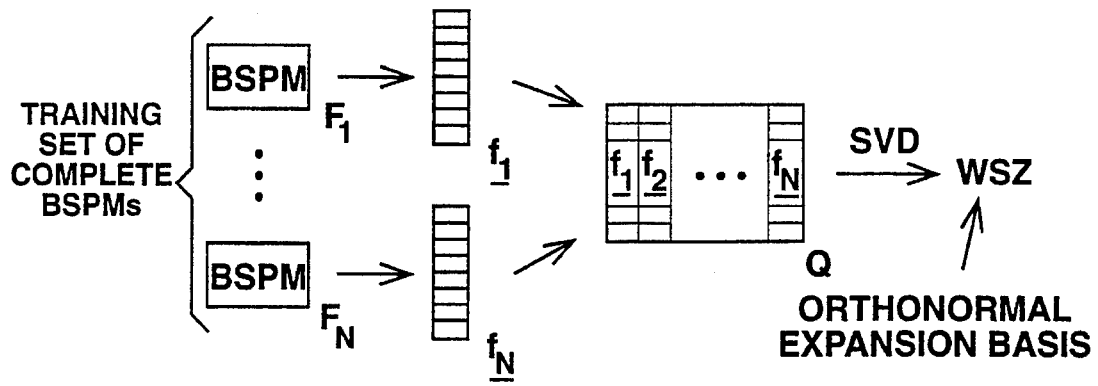
FIG. 3. The reconstruction procedure: At the first stage, the eigenfunctions are calculated from the complete measurements of the BSPM, from all members of the training set. Then for every new subject being measured, i.e. a member of the test set, level-crossing instants are used for constructing the linear system of equations. The solution provides decomposition coefficients for that particular subject, which later are used for the reconstruction of his complete BSPM.
Figure 3:
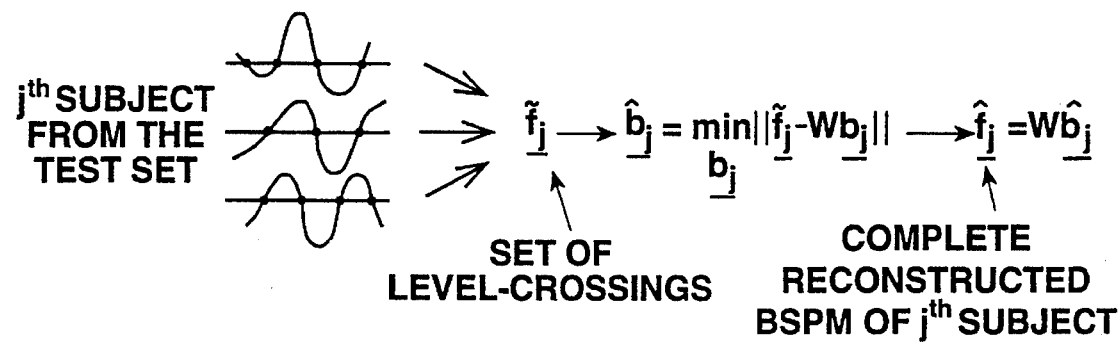

The whole procedure is summarized in FIG. 3.

The complete BSPM data of 281 patients and normal subjects, recorded at Case Western Reserve University (CWRU), are utilized here to study the effects of reconstruction from level-crossings information. The BSPM recording system uses 180 ECG electrodes, placed in the form of a rectangular grid over the thorax, and referenced to the Wilson Central Terminal. Each ECG signal is filtered by a 0.5–200 Hz analog band-pass filter and sampled at 500 Hz for approximately 1 sec, so that the data of at least one complete heart beat are included. The stored measurements are inspected visually, and noisy or otherwise distorted maps are eliminated from the data pool. All the processing is done on a VAX-2000 workstation.

In the present study, only the QRS portion of electrocardiograms is used. It is identified in lead $V_6$, by detecting the peak of R wave and taking 27 backward and 36 forward samples. Accordingly all the ECG values outside this range are set to zero, resulting in 128 mS records. It was assured that these records contain entire measurements of QRS.

The study population—The data from the 281 subjects are divided into two sets—a "training set" and a "test set". The "training set" includes 200 subjects which have been diagnosed previously and separately as follows: 65 normals, 65 patients with WPW syndrome, 10 subjects diagnosed as various forms of CAD, 40—ASD and 20—VSD patients. The additional 81 subjects comprise the "test set", which has the same distribution of pathologies as that of the "training set".

Construction of orthonormal expansion basis—In order to obtain a set of basis functions for the reconstruction algorithm, the covariance matrix is constructed, consisting of 200 subjects from "training set" each of 64 (time samples) by 180 (electrodes)=11520 samples. All measurements have been aligned to the moment of R wave peak. Then the covariance matrix is decomposed by the SVD procedure.

Figure 4:
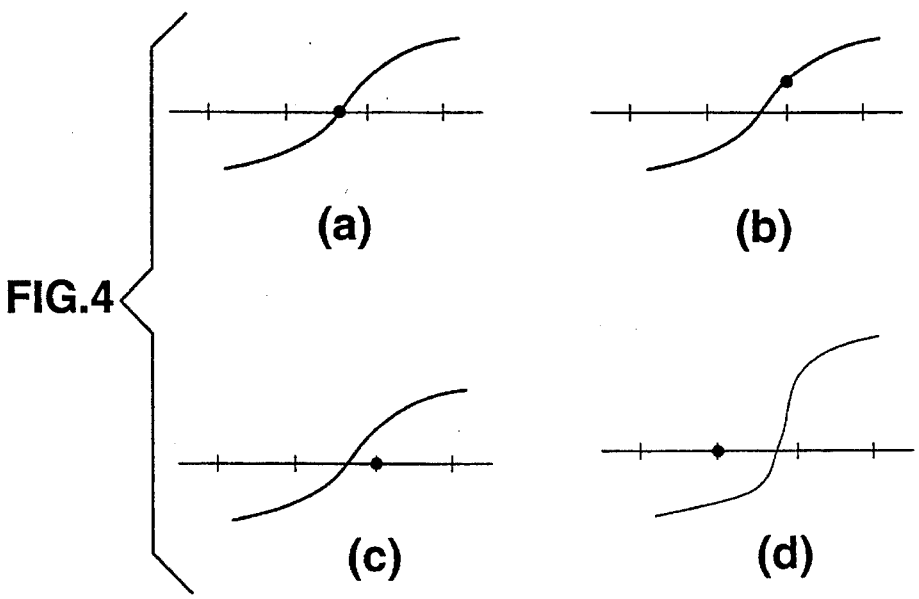
FIG. 4. Different ways of level-crossing measurement. The ticks represent a selected sampling interval.

Calculation of LC—In the second set, (the "test set"), only LC instants at various thresholds are measured, for later use in the reconstruction procedure. The LC measurements are simulated here from the measured BSPMs in two different ways, as reflected in the FIG. 4. Firstly, the quality of the reconstruction from LC has been studied for an "ideal system" (i.e. the system with infinite sampling resolution). In order to simulate such a system, the LC instants are taken as the actually sampled values of BSPMs nearest to the LC (as in FIG. 4b). In the case where the threshold level is zero (i.e. zero-crossings) the linear system of equations based on (7) is found to be nearly homogeneous. Secondly, the LC instants are simulated as discrete sampling times closest to the actual measurement of crossing moment (FIG. 4c). This does not produce exact crossing instants, but rather an approximation of them. It makes possible the study of the effects of finite resolution sampling, as well as the consequences of noisy measurements. (In the case of ZC, the linear system of equations (7) is of a homogeneous type). The theoretical aspects of erroneous sampling were studied by Zeevi et al., [24].

FIG. 4d shows the extreme situation where the approximation of LC instants, made according to the second method, has led to an erroneous value of LC.

Error estimation—The quality of the reconstruction from level-crossing instants depends on various factors. In order to assess the quality of a reconstruction, some error measures are defined. The RMS criteria is introduced as follows:

$$e_{RMS} = \sqrt{(\Sigma (f_j - \hat{f}_j)^2)/N}$$

where $f_j$ is the whole 3-D discretized original BSPM sequence, comprising of N points, and $\hat{f}_j$ is its reconstruction. The RMS measure provides the average error for each individual subject and is expressed in μV.

On the other hand, since the LC method is very sensitive to the amplitude of the signals and thus to the amplitude of the maps, the correlation coefficient is introduced as an alternative to the RMS measure. This measure serves more to reflect the differences in the patterns between the measured and reconstructed BSPM surfaces, independent of their magnitudes.

$$\rho = f_j * \hat{f}_j / (|f_j| |\hat{f}_j|)$$

In addition, the mean error values for the map sequences of the whole test set are defined as the average RMS error and correlation for all subjects comprising this set.

COMPRESSION OF ORIGINAL AND/OR RECONSTRUCTED BSPM

It will thus be seen that sequences of annuli, evaluated from a series of maps, adequately preserve the information contained in the shape and movement of the surface potential distribution as a function of time.

Further processing steps are required to perform the data reduction procedure correctly. A two-dimensional weighted average of nearest neighbours interpolation is carried out to generate a map of 44×72 pixels. Eight neighbours' amplitude values are weighted according to 1/(square of D), where D is the distance between the desired point and the neighbour point.

The generation of a series of annuli from series of maps is performed in the following way:

(a) Each map is thresholded twice at two chosen levels of different potentials.

(b) Each thresholded image is converted to a binary format. (Two binary images are therefore formed from each map.)

(c) The annuli are created by subtracting one binary image from the other.

These three steps require image processing techniques to perform the data reduction procedure correctly and to create the annuli. The processing includes amplitude thresholding and edge detection. A binary image is then created by multiplication with a suitable mask. The whole procedure is then performed separately for the negative voltage section of each map. The data reduction procedure is performed rapidly and is also significant in saving CPU time and storage capacity; it therefore may be easily implemented in any real-time protocol.

The thresholding procedure requires the selection of two parameters: the height of the basic thresholding level, and the difference between the two levels. The basic level is determined by the noise level, which is computed as the average RMS value of four electrodes at the inferior right midaxillary line. These electrodes are far from myocardial electrical sources and can hardly detect any ECG information. The highest level found in the whole study group is taken as the noise level. The basic level is then chosen as twice the noise level, to minimize noise without losing the fine details. This produces a threshold level which is 14 percent of the maximum normalized positive peak potential (the R wave).

The choice of thresholding at such a low level is also important in obtaining an annulus during a major part of the heart cycle. The difference between the basic thresholding level and the second level is the second parameter to be chosen. The difference (in mV) is selected empirically to enable further processing of the annulus. The requirement is for an accurate estimation of the gradient near the basic level, and therefore the difference between the two levels should be as small as possible. This requirement is limited by the spatial resolution and by the demand for a suitable width of annulus (at least one pixel). A difference of 6 percent is taken between the two threshold levels; the second threshold level is therefore 20 percent of the positive peak potential.

FEATURES EXTRACTED FROM BSPM AND/OR ANNULI SEQUENCES FOR CLASSIFICATION AND DISPLAY

Feature Extraction

Quantitative analysis of the shape and movement of the annuli series is made simpler by defining a set of features that characterizes the annuli. This set is calculated as a function of time, and is expected to represent the dynamic nature of the annuli. The features, or indices, extracted from the annuli are:

(i) times of appearance and disappearance of the annuli and annuli duration. These indices are highly dependent on the threshold level.

(ii) the loci in three-dimensional space, drawn by the centre of mass of the annuli during the heart cycle. The three-dimensional loci (two-dimensional torso coordinates and time) represent the advance of the activation front inside the muscle. This may be an important feature for discriminating between normal and abnormal heart activity, as the sequence of activation changes in an abnormal tissue and may draw a different trajectory.

(iii) The two-dimensional cross-correlation coefficient estimator, evaluated for the sequence of annuli (between each consecutive pairs of annuli) as a function of time, to produce an estimate of the cross-correlation coefficients series.

$$\rho(r,s) = \frac{1}{\sigma_k \sigma_{k+1}} \times \frac{\sum_{i=0}^{N_k-r-1} \sum_{j=0}^{N_{k+1}-s-1} (f_k(i,j) - \overline{a_k})(f_{k+1}(i,j) - \overline{a_{k+1}})}{(N_k - r)(N_{k+1} - s)} \quad (2)$$

where $\rho(r, s)$ is the cross-correlation coefficient (for lags r and s, r and s are the lags in the i and j directions, respectively, $f_k(i,j)$ is the kth image values (0 or 1), $\overline{a}_k$ is the average value of the kth image, $\sigma_k$ is the standard deviation of the kth image, $N_k$ is the number of points in the kth image and k= 1,2, . . . The cross-correlation coefficients series is expected to express the changes in annulus shape and area in the vicinity of peak QRS. Thus low values of the coefficients are expected in that region of rapid changes.

(iv) A measure of the estimated activation wave front displacement (which is also a measure of estimated velocity of the annulus) is achieved by calculating the distance between the centres of mass of consecutive maps.

RESULTS

In FIG. 5., an example of reconstruction for a particular subject is shown for the 60 most significant electrodes. The reconstruction procedure is based on (8), and 80 eigenfunctions are utilized for composing the above linear system of equations. As empirically found, 80 eigenfunctions which relate to 80 unknowns, is about the optimal number of eigenfunctions required for reconstruction.

The sensitivity of the reconstruction to different threshold values is shown in FIG. 6. A combined plot of RMS error and the number of the level-crossing instants obtained for a representative BSPM sequence of some subject is shown as a function of the chosen level. In general, the reconstruction quality is related to the number of crossing instants. As this number grows, meaning an increase in the number of equations of the linear system (7), the description of the system becomes more and more overdeterministic, which leads to a more robust determination of the decomposition coefficients. However, the larger number of crossing instants obtained when approaching the zero-level, does not lead to an optimal value for the RMS error, because more and more noise is measured at these critical voltage values. The crossing levels of ±100 μV together produce about 350 sampling points, about 4–4.5 times the number of unknowns (decomposition coefficients), which is probably the required overdeterminicity for such a system. (It is of interest to note that a similar factor is reported for a reasonable reconstruction, using ZC reconstruction methods [18,20]). Out of those two values (±100 μV), the −100 μV level is slightly preferable, since at this level there are significantly more sampling points, from the Q and S waves. When the −100 μV threshold is used, it leads to a 279 μV mean RMS reconstruction error, which is too high for any practical system. It has been found that a large portion of this error is due to the difficulty in matching the two BSPM surfaces (original and estimated), as amplitude information is lacking in the LC data.

The contribution of the additional amplitude information to the quality of the reconstruction is studied by specifying some electrodes to measure different crossing levels. At first, every second electrode is set to measure level-crossings at 1500 μV, while the remaining electrodes measure at the original −100 μV level. Afterwards, the threshold is gradually lowered to −1500 μV. Each time, the reconstruction is repeated. The results of the above procedure are shown in FIG. 7.

Next, different combinations of various threshold levels are tested and the best tradeoff between the system complexity and performance has been empirically found. The following results are shown for the best tradeoff, in which the system consists of four different thresholds: ±100 μV, ±500 μV each assigned to a different array of 45 electrodes, where each one of the intermittent arrays is spread out over the entire thorax. (FIG. 8 reflects this situation). The mean value of RMS error for all the different pathological groups is 136 μV, while the mean RMS error for each group by itself is: NORM—86 μV, WPW—144 μV, CAD—76 μV, ASD—151 μV and VSD—219 μV. FIG. 9 displays a histogram of the RMS error of the test group population. An example of the original versus the reconstructed maps (3 snapshots through the QRS cycle), of a representative normal subject, is shown in FIG. 10. The example was selected to display reconstructed maps with typical reconstruction error, similar to the mean RMS error for the group of normals. It has been observed that the disparities in the maps with higher RMS error are due to the amplitude differences, while there is a close correspondence between a reconstructed spatial waveform and the original signal. High correlation coefficients also reflect this situation: NORM—0.946, WPW—0.92, CAD—0.938, ASD—0.862, VSD—0.883. with a mean group correlation of 0.909 between the reconstructed and original BSPMs.

In order to study the effect of the intra-group variability (as demonstrated by the different RMS error values), the BSPMs of all the normals have been removed from the training set. Then the SVD is computed once again and a new set of eigenfunctions is obtained. When reconstructing the BSPM of the members of the test set on the new basis, the following results are obtained: RMS error for NORM—90 μV, WPW—147 μV, CAD—84 μV, ASD—150 μV, VSD—237 μV. In this case, the mean RMS error is larger and every group is almost equally affected by the elimination of normals from the training set. It is interesting to note that the results for the group of normal subjects in the test set are not affected by this procedure more severely than any other group. This is probably due to the averaging process (which is inherent to the computation of the SVD) of the various disease groups, which produces mean eigenfunction waveforms that resemble the corresponding eigenfunction waveforms of normals.

On the other hand, when WPW patients (65) are eliminated from the training set and then reconstruction performed as before, the following RMS errors are obtained: NORM—83 μV, WPW—214 μV, CAD—82 μV, ASD—162 μV, VSD—229 μV. The mean RMS error of the WPW group grows significantly higher than the mean RMS error of each of the other disease groups. FIG. 11 summarizes the results of the three different experiments. It is demonstrated that in order to reconstruct BSPM waveforms for the various groups, the training set should be as large as possible, and should contain various types of the more important heart diseases.

In order to create a robust eigenfunction basis, the training set must include as much a-priori measured data as possible. However, since technical considerations, such as computer memory size and CPU time, are bound to limit the data base size, the "training set" must include similarly sized groups of all the various pathologies.

The optimal number of eigenfunctions required for a reconstruction is found by studying the mean RMS error as a function of the number of eigenfunctions. It may be seen (from the plot in FIG. 12) that the number of eigenfunctions required for reconstruction from level-crossing instants is about 80. While other authors [10] selected the number of eigenfunctions around 40 we have chosen to double this number since our set of data includes very wide range of patients. For more than 80 eigenfunctions, the overdeterminicity of the linear system of equations (7), i.e. number of equations (level-crossing instants) per number of unknowns (coefficients of eigenfunctions), is on average less than 4 (for the system of 180 electrodes), and therefore is too small for a proper reconstruction.

Next, the effects of finite resolution in sampling have been studied, as well as the influence of measurement noise. To simulate these phenomena, the situation depicted in FIG. 4c is utilized. Despite a significant increase of additional noise (which is expressed as an inexact registration of LC times), with a variance of 500 μS, the mean RMS reconstruction error increases by only 7%, to 146 μV. This result is very important for the practical implementation of the level-crossing BSPM system, since measurement noise is always present and can not be completely avoided.

One way to further improve the reconstruction quality is to incorporate a number of regular electrodes and use their complete ECG morphology in the reconstruction procedure. It is sufficient to include just very few additional electrodes (e.g. the standard ECG three-lead system). It is observed that the improvement in the mean RMS error reaches saturation very fast with the increase in the number of regular electrodes. The addition of the complete recording of the single $V_6$ electrode leads to a 6% decrement in RMS error. The second additional electrode $V_2$ further decreases the error by 3%, but then as more regular electrodes are added their contribution becomes less and less significant. The improvement in reconstructing the BSPM by adding such electrodes is affected locally, i.e. in the immediate vicinity of the regular electrode, and has little influence on the overall pattern of the BSPM. This is despite the fact that each such electrode introduces about 60 additional sampling points (over the QRS), i.e. about a 20% increase in the number of equations in system (7). This supports the conclusion that the main factor for good reconstruction is homogeneous distribution of sampling instants over the entire BSPM domain.

DESCRIPTION OF A PREFERRED EMBODIMENT

The invention, and its advantages, will be better understood by reference to FIG. 13 of the drawings illustrating an existing BSPM system, and to FIG. 14 which illustrates a novel BSPM system in accordance with the present invention. The prior art system illustrated in FIG. 13 details in particular the analog stages which are replaced by the novel system as illustrated in FIG. 14. It wil be seen that the novel system illustrated in FIG. 14 enables a very significant reduction to be made in the amount of accumulated data, thereby facilitating analysis and display of long, continuous measurements.

FIG. 15 further describes the novel method, wherein it will be seen that, in the measurements performed for each patient requiring electrocardiographic diagnosis, each channel registers only the time intervals when the incoming potentials on the patient's torso cross a preset level. The values in matrix W are stored as a compressed data base.

In FIG. 16, the left diagrams illustrate the ECG potentials measured during one heartbeat by 180 electrodes around the torso for two patients; and the right diagrams illustrate the potentials reconstructed for measuring only the cross times for the same patients and the same heartbeat. The upper sets of diagrams are examples from a patient for whom the reconstruction error was small; and the diagrams in the lower set are examples from a patient for whom the reconstruction error was relatively large.

FIG. 17 illustrates the sequences of three maps presented by 2-D isopotential lines as measured by the novel method over the whole torso. The left diagrams are original maps calculated from ECG measurements by the 180 electrodes using commercial equipment; and the right diagrams are reconstructed maps for the same patient, and for the same time instants, calculated by the above described procedure from the time intervals measured in each electrode when the incoming potentials cross a preset level.

FIG. 18 illustrates sequences of four 3-D potential maps as measured over the whole torso. The left diagrams are maps calculated from ECG measurements by the 180 electrodes using commercial equipment; and the right diagrams are reconstructed maps for the same patient, and for the same time instants, calculated by the above described procedure from the time intervals measured in each electrode when the incoming potentials cross a preset level.

FIG. 19 illustrates typical annuli sequence of normal subject (4 ms apart, lower part a-1) and WPW patient (8 ms apart, upper part a-1) measured during the QRS period. (Amplitude values are normalized and threshold levels are selected to be 14 percent and 18 percent of the maximum normalized positive peak.)

FIG. 20 illustrates cross-correlation coefficients series as a function of time during the QRS-wave period (positive potential section of the maps). (a) four examples from the normal group; (b) WPW patient; (c) MI patient; (d) and (e) AS patients.

Cross-correlation coefficients series provide an estimate of the resemblance between successive annuli. FIG. 20 depicts fluctuations of the coefficients series as a function of time. All plots of the normal group (during the QRS) have two main peaks; one between 14 and 18 ms (with one exception at 22 ms) and the second between 32 and 44 ms. The second main peak, in most cases, contains a small depression of 4–6 ms in length. The cross-correlation coefficients reach values between 0.78 and 0.94 at the peaks with low values between 0.15 and 0.53 at the minima. WPW patients are characterized by consistently high values of coefficients with no distinct peaks. MI patients do exhibit two peaks but with the first peak appearing at 34 ms. The peaks are delayed with respect to the normal cases. AS patients exhibit various patterns which differ from each other, although, in two cases, two main peaks are observed, as for the normal patients. The graphs of these two patients are characterized by high coefficient values at the longer timing intervals.

DISCUSSION

In this study, an algorithm has been described for the reconstruction of the original BSPM function from the partial information obtained from its level-crossings. The BSPM is considered here as a three-dimensional, dynamically changing, spatial process. In this way, precise values of LC instants are measured by detecting the times when the incoming ECG signal crosses a given threshold. In order to make the reconstruction feasible, the Karhunen-Loeve expansion (as opposed to Direct Fourier and iterative procedures used so far) is utilized here, thus producing a compact representation of the BSPM. The BSPM is treated as samples of a random process, thus limiting the reconstruction procedure to certain restricted classes of signals.

The proposed method presents a different approach to the BSPM measurement system. Instead of reducing the number of electrodes, as done in previous studies [7–11], it utilizes threshold electrodes which eventually could lead to simplification of the analog system requirements, such as multiplexing, amplifying, filtering, sampling and storage units. Noise reduction may be achieved as well, since the measuring components which are essentially voltage comparators, can be built-in at the electrodes themselves and thus be placed in the immediate vicinity of the body. The information in such a system is transmitted in a digital form, thus eliminating cross-talks and the interference noise. Also, as a byproduct of the reconstruction algorithm, the K-L decomposition coefficients are calculated, and may be used without additional computation effort for the purpose of classification.

When a single threshold level is selected for all electrodes, the best performance is obtained by setting this level to $-100$ μV. At this level, the largest number of LC instants is measured without being significantly affected by the system noise. However, a substantial improvement is achieved when different electrodes are set to different threshold levels, thus implicitly providing some amplitude information. An average RMS error of 136 μV (nearly half) and correlation of 0.909 are obtained when four levels ($\pm 100$ μV, $\pm 500$ μV) are utilized at four rectangular grids of electrodes, as shown in FIG. 8.

The results achieved so far allow good reconstruction of the BSPM signal during the QRS wave. However due to the average RMS error of 136 μV the proposed procedure does not allow good reconstruction of low level features of the maps, e.g., early negative poles in WPW, subtle changes in STT potentials. It is quite clear that better performance may be gained if more than four thresholds were chosen, and moreover if their levels were varied according to the location on the chest surface. Region with expected low potentials should be assigned lower threshold levels and in contrary sites with high potentials should include in addition to electrodes assigned to low thresholds also electrodes assigned to higher levels of measurement. Even better performance may be gained by adaptively changing the threshold levels from patient to patient. One of the possible ways to change the threshold is in accordance to the rate of LC measured in that electrode. Generally, levels with the highest rates of crossings should be preferred, except within the region of noise.

The number of electrodes (180) selected for the present system is in agreement with existing regular BSPM systems. The reduction of the number of electrodes, as suggested by some authors [7–11], is compromising the spatial resolution of the system; here such a reduction will also cause deleterious effects in the reconstruction. On the other hand, since each measuring channel is extremely simple, the incorporation of additional electrodes does not increase the complexity of the system, but can improve further the quality of the measurement.

The solution of the linear system of equations (7) has been made in the least-squares sense. The regularized solutions similar to these cited in [7], do not lead to better estimations of decomposition coefficients, since unlike the inverse problem where the regularization serves as a restriction on the function space, here a constrained problem is already defined by formulating it in a framework of Karhunen-Loeve expansion. This formulation assumes that the BSPM function is best described by the eigenfunctions of the appropriate random process.

Optimal performance of the system is achieved when the reconstruction procedure is performed on a basis in the range of 80 eigenfunctions. This number is 4–4.5 times lower than the average number of LC instants produced by the system. It is again observed as a golden standard for the required overdeterminicity of the linear system of equations used in the reconstruction procedures from LC [18,20]. For less than 80 eigenfunctions, small details are lost in the reconstructed BSPMs, while for larger numbers the overdeterminicity is low.

Two hundred subjects comprise the training set for the algorithm. This number of subjects is supposed to be sufficient to generate a representative set of eigenfunctions. Though the number of sample points for each patient is very large (p·t=11520) there is a huge redundancy in the data of the BSPM—both time redundancy and spatial redundancy due to oversampling. The size of the training set, therefore, does not have to be extremely large. In order to test whether the size of our training set is sufficient, as well as whether the distributions of the normal BSPM and pathological BSPM are representative, we have calculated the average RMS error of reconstruction of the whole study set—but this time from the complete BSPM measurement and not form their LC: the average RMS error was found to be 77.6 µV and the average correlation 96.5, very similar to the value of 73 µV as reported by others [10]. On the other hand, when studying FIG. 10, the average RMS errors for some of the groups of pathologies (WPW, ASD and especially VSD) are higher than that of the normal group, which implies that these groups were not well represented in the training set. Therefore, the size of the training set should be as large as possible and the various pathologies should be evenly distributed over the training set.

The average RMS error of reconstruction of the test set increases to 136 µV when LC are used. This value can be reduced by several modifications which were discussed earlier, i.e., using different threshold levels at different sites, modifying the levels adaptively for each patient etc. These modifications will increase somewhat the complexity of the system. A simple modification that improves the results may be made by measuring in 1–3 electrodes the regular ECG data. The amplitude information obtained improves the reconstruction from the LC, with a reduction of the average RMS error to about 120 µV. This modification is beneficial, since it allows to compare the reconstructed waveforms to those measured by the regular electrodes.

The overall system performance is relatively insensitive to moderate levels of noise in the LC measurement. This was demonstrated by the introduction of errors in the range of 20–30 µV. This fact is very important for the compression of the BSPM, since in any practical BSPM system, there is noise associated with the level-crossing measurement. The relative robustness of the above scheme for reconstruction from level-crossings is due to the compact representation of ECG signals over the whole signal space. This becomes evident when comparing to the other existing methods such as direct Fourier transform and iterative procedures. This data compression technique preserves the dynamic changes present in the sequence of the BSPM, and therefore describes the dynamics of the underlying process well. The method is also sensitive to both the repolarization and depolarization periods and is not limited to a specific kind of disease. The use of annuli sequences instead of the whole BSPM sequences can facilitate display and visual inspection of the maps. Because of the enormous amount of information produced by the measurement of BSPM, no simple and cheap solution is available today for displaying the data in real time or in a movie-like sequence of maps. The features extracted from the annuli sequences have been calculated as a function of time to express the dynamic nature of the process. Four different groups of subjects have been investigated: normal patients, AS, WPW, and MI patient groups. The appearance and time duration of the annuli sequence have been measured, as well as the loci of the centres of mass of the annuli sequence, cross-correlation coefficients series between successive annuli in a sequence and the distance between centres of mass in successive annuli (which is also a measure of the estimated annulus velocity), all during the QRS-wave period and separately during the T-wave period. These features can characterize quantitatively the dynamic nature of the sequence. The features have been found to be similar for each group. Thus a classification protocol can be established to distinguish between the different groups with a high level of confidence.

REFERENCES

1. D. M. Mirvis, Current status of body surface electrocardiographic mapping, *Circulation*, vol.75, pp.684–688, 1987.
2. R. C. Barr and M. S. Spach, Inverse calculation of QRS-T epicardial potentials from body surface potential distributions for normal and ectopic beats in the intact dog, *Circ. Res.*, vol.42, pp.661–675, 1978.
3. B. J. Messinger-Rapport and Y. Rudy, Computational issues of importance to the inverse recovery of epicardial potentials in a realistic heart-torso geometry, *Math. Biosciences*, vol.97, pp.85–120, 1989.
4. L. F. Favella, Mathematical foundations of ECG map reconstruction, *Cybernetics & Systems: Int. J.*, vol. 11, pp.21–66, 1980 .
5. L. Horan, N. Flowers and D. Brody, Principal factor waveforms of the thoracic QRS complex, *Circ. Res.*, vol.15, pp.131–138, 1964.
6. N. Ahmed and K. R. Rao, *Orthogonal transforms for Digital Signal Processing*. Berlin, Germany: Springer-Verlag, ch. 9, 1975.
7. R. C. Barr, M. S. Spach and G. S. Herman-Giddens, Selection of the number and positions of measuring locations for electrocardiography, *IEEE Trans. on BME*, vol.18, No.2, pp.125– 138, 1981.
8. R. L. Lux, A. K. Evans, M. J. Burgess, R. F. Wyatt and J. A. Abildskov, Redundancy reduction for improved display and analysis of body surface potential maps. I. Spatial compression, *Circ. Res.*, vol.49, pp.186–196, 1981.
9. A. K. Evans, R. L. Lux, M. J. Burgess, R. F. Wyatt and J. A. Abildskov, Redundancy reduction for improved display and analysis of body surface potential maps. II. Temporal compression, *Circ. Res.*, vol.49, pp.197–208, 1981.

10. G. J. H. Uijen, A. Heringa and A. Van Oosterom, Data reduction of body surface potential maps by means of orthogonal expansions, *IEEE Trans. on BME*, vol.31, pp.706–714, 1984.

11. R. L. Lux, C. R. Smith, R. F. Wyatt and J. A. Abildskov, Limited lead selection for estimation of body surface potential maps in electrocardiography, *IEEE Trans. on BME*, vol.25, pp.270–276, 1978.

12. N. Balossino, L. F. Favella and M. T. Reineri, ECG map filtering by means of spherical harmonics: A simple approximation and results, *Cybernetics. and Systems: Int. J.*, vol.15, pp.1–40, 1984.

13. B. J. Messinger-Rapport and Y. Rudy, Regularization of the inverse problem in electrocardiography: a model study, *Math. Biosciences*, vol.89, pp.79–118, 1988.

14. H. B. Voelcker, Toward a unified theory of modulation-Part II: Zero manipulation, *Proc. IEEE*, vol.54, pp.735–755, 1966.

15. B. J. Levin, Distribution of zeroes of entire functions. Providence, R.I.: Amer. Math. Soc. Transl., 1980.

16. A. A. G. Requicha, Zeroes of entire functions: theory and engineering application, Proc. *IEEE*, vol.68, pp.308–328, 1980.

17. B. F. Logan, Information in the zero-crossings of bandpass signals, *Bell Tech. J.*, vol.56, pp.487–510, 1977.

18. D. Rotem and Y. Y. Zeevi, Image reconstruction from zero-crossings, *IEEE Trans. on ASSP*, vol.34, pp.1269–1277, 1986.

19. S. R. Curtis and A. V. Oppenheim, Reconstruction of multi-dimensional signals from zero-crossings, *J. Optical Soc. Amer.*, vol.4, pp.221–231, 1987.

20. S. R. Curtis, A. V. Oppenheim and J. S. Lim, Signal reconstruction from fourier transform sign information, *IEEE Trans. on ASSP*, vol.33, p.643–657, 1985.

21. A. Papoulis, A new algorithm in spectral analysis and band-limited extrapolation, *IEEE Trans. on Circ. & Syst.*, vol.22, pp.735–743, 1975.

22. D. C. Youla and H. Webb, Image restoration by the method of convex projections: Part I-Theory, *IEEE Trans. Med. Imaging*, vol.MI-I, pp. 81–94, 1982.

23. G. E. Forsythe, M. A. Malcolm and C. B. Moler, *Computer methods for mathematical computations*. Englewood Cliffs, N.J.:Prentice-Hall, ch. 9, 1977.

24. Y. Y. Zeevi, A. Gavriely and S. Shitz, Image representation by zero and sine-wave crossings. *J. Optical Soc. Amer.*, vol.4, pp.2045–2060, 1987.

What is claimed is:

1. A method of analyzing the electrical activity of the heart by Body Surface Potential Mapping (BSMP), comprising, applying an array of electrodes over the thoracic region of a subject's body for producing measurements of the electrical signals generated in said thoracic region, and processing said measurements for indicating certain electrical events in the subject's body; characterized in utilizing said array of electrodes to measure only the times of crossing of the electrical signals over a preset threshold.

2. The method according to claim 1, wherein the processing of said measurements includes the following steps:

(a) estimating the covariance matrix of random processes from the measurements by said array of electrodes;

(b) decomposing said covariance matrix into the eigenfunction basis;

(c) evaluating, from a partial set of said measurements for the respective subject, the coeffecnt of a linear combination of computed eigenfunctions; and (d) expanding said computed eigenfunctions to obtain a complete reconstruction of the BSPM.

3. The method according to claim 2, wherein the reconstruction of the BSPM in step (d) is performed by dividing the array of electrodes into a plurality of intermittent grids, and utilizing a corresponding number of the threshold levels, one for each of said grids.

4. The method according to claim 3, wherein said reconstruction is performed by dividing the array of electrodes into four intermittent grids and utilising four threshold levels, one for each of said grids.

5. A method analyzing the electrical activity of the heart by Body Surface Potential Mapping (BSMP), comprising, applying an array of electrodes over the thoracic region of a subject's body for producing measurements of the electrical signals generated in said thoracic region, and processing said measurements for indicating certain electrical events in the subject's body; characterized in that the processing of said measurements incudes the following steps:

(a) estimating the covariance matrix of random processes from the measurements by said array of electrodes;

(b) decomposing said covariance matrix into the eigenfunction basis;

(c) evaluating from a partial set of said measurements for the respective subject, the coefficient of a linear combination of computed eigenfunctions; and (d) expanding said computed eigenfunctions to obtain a complete reconstruction of the BSPM.

6. The method according to claim 5, further characterized in that said array of electrodes are utilized to measure only the times of crossing of the electrical signals over a preset threshold.

7. The method according to claim 6, wherein said reconstruction of the BSPM is performed by dividing the array of electrodes into a plurality of intermittent grids, and utilizing a corresponding number of the threshold levels, one for each said grids.

8. The method according to claim 7, wherein said reconstruction is performed by dividing the array of electrodes into four intermittent grids and using four threshold levels, one for each of said grids.

9. The method according to claim 5, wherein said measurements of the thoracic region of the subject's body, and said reconstruction of the BSPM, are thresholded twice at two chosen levels, and annuli are calculated for storage, display, and further processing.

10. Apparatus for analyzing the electrical activity of the heart by Body Surface Potential Mapping (BSPM), comprising:

an array of electrodes placeable over the thoracic region of a subject's body;

measuring means for producing measurements of the electrical signals generated in said thoracic region as detected by said array of electrodes;

and processor means for procesing said measurements for indicating certain electrical events in the subject's body;

characterized in that said measurement means measures only the times of crossing of the electrical signals over a preset threshold as detected by said array of electrodes.

11. The apparatus according to claim 10, wherein said processor means includes:

(a) means for estimating the covariance matrix of random processes from the measurements by said array of electrodes;

(b) means for decomposing said covariance matrix into the eigenfunction basis;

(c) means for evaluating, from a partial set of said measurements for the respective subject, the coefficent of a linear combination of computed eigenfunctions; and (d) means for expanding said computed eigenfunctions to obtain a complete reconstruction of the BSPM.

12. The apparatus according to claim 11, wherein said means (d) performs said reconstruction by dividing the array of electrodes into a plurality of intermittent grids and utilizing a corresponding number of threshold levels, one for each of said grids.

13. The apparatus according to claim 12, wherein said reconstruction is effected by four intermittent grids and by utilizing four threshold levels, one for each of said grids.

14. Apparatus for analyzing the electrical activity of the heart by Body Surface Potential Mapping (BSPM), comprising:

an array of electrodes placeable over the thoracic region of a subject's body;

measuring means for producing measurements of the electrical signals generated in said thoracic region as detected by said array of electrodes;

and processor means for processing said measurements for indicating certain electrical events in the subject's body;

characterized in that said processor means includes:

(a) means for estimating the covariance matrix of random processes from the measurements by said array of electrodes;

(b) means for decomposing said covariance matrix into the eigenfunction basis;

(c) means for evaluating, from a partial set of said measurements for the respective subject, the coefficent of a linear combination of computed eigenfunctions; and (d) means for expanding said computed eigenfunctions to obtain a complete reconstruction of the BSPM.

15. The apparatus according to claim 14, further characterized in that said electrical measuring circuit for each electrode measures only the times of crossing of the electrical signals over a preset threshold.

16. The apparatus according to claim 15, wherein said means (d) performs said reconstruction by dividing the array of electrodes into a plurality of intermittent grids and utilizing a corresponding number of threshold levels, one for each of said grids.

17. The apparatus according to claim 16, wherein said reconstruction is effected by four intermittent grids and by utilizing four threshold levels, one for each of said grids.

* * * * *